US007485627B2

(12) United States Patent
Raz et al.

(10) Patent No.: US 7,485,627 B2
(45) Date of Patent: *Feb. 3, 2009

(54) METHOD FOR TREATING INFLAMMATORY BOWEL DISEASE AND OTHER FORMS OF GASTROINTESTINAL INFLAMMATION

(75) Inventors: Eyal Raz, Del Mar, CA (US); Daniel Rachmilewitz, Tel Aviv (IL)

(73) Assignees: The Regents of the University of California, Oakland, CA (US); Tel Aviv Sourasky Medical Center, Tel Aviv (IL)

( * ) Notice: Subject to any disclaimer, the term of this patent is extended or adjusted under 35 U.S.C. 154(b) by 763 days.

This patent is subject to a terminal disclaimer.

(21) Appl. No.: 10/412,151

(22) Filed: Apr. 11, 2003

(65) Prior Publication Data
US 2003/0176389 A1  Sep. 18, 2003

Related U.S. Application Data

(63) Continuation of application No. 09/791,500, filed on Feb. 22, 2001, now Pat. No. 6,613,751.

(60) Provisional application No. 60/184,256, filed on Feb. 23, 2000.

(51) Int. Cl.
*A61K 31/70* (2006.01)
(52) U.S. Cl. .............. 514/44; 536/23.1; 435/320.1; 435/325; 435/455
(58) Field of Classification Search ............ None
See application file for complete search history.

(56) References Cited

U.S. PATENT DOCUMENTS

| 5,716,615 | A | * | 2/1998 | Cavaliere Vesely et al. | 424/93.4 |
|---|---|---|---|---|---|
| 5,736,524 | A |  | 4/1998 | Content et al. | |
| 6,194,388 | B1 |  | 2/2001 | Krieg et al. | |
| 6,207,646 | B1 |  | 3/2001 | Krieg et al. | |
| 6,214,806 | B1 |  | 4/2001 | Krieg et al. | |
| 6,218,371 | B1 |  | 4/2001 | Krieg et al. | |
| 6,228,371 | B1 |  | 5/2001 | Nano et al. | |
| 6,239,116 | B1 |  | 5/2001 | Krieg et al. | |

FOREIGN PATENT DOCUMENTS

| WO | WO 98/18810 |  | 5/1998 |
|---|---|---|---|
| WO | WO 00/01851 | * | 1/2000 |
| WO | WO 00/01851 A1 |  | 1/2000 |
| WO | WO 01/22972 A2 |  | 4/2001 |
| WO | WO 01/22990 A2 |  | 4/2001 |

OTHER PUBLICATIONS

Obermeier et al. Clin Exp Immunol. Nov. 2003 134:217-224.*
Baert et al. Gastroenterology 1999;116:22-28.*
Shimosato et al. Animal Science Journal (2004) 75, 377-382.*
Obermeier et al. Clin Exp Immunol 2003 134:217-224.*
Goldberg et al 2000 Immunology Letters.73:13-18.*
Yamada et al 2002 Journal of Immunology p. 5594.*

Krieg, "Mechanisms and applications of immune stimulatory CpG oligodeoxynucleotides" Biochimica et Biophysica Acta. Gene Structure and Expression, Elsevier Amsterdam, NL, vol. 1489, No. 1, Dec. 10, 1999, pp. 107-116.
Krieg "The role of CpG motifs in innate immunity" Current Opinion in Immunology, Current Biology, Ltd. vol. 12, No. 1, Feb. 1, 2000, pp. 35-43.
Selby et al. (2000) "Pathogenesis and therapeutic aspects of Crohn's disease." *Veterinary Microbiology*, vol. 77:505-511.
Asseman et al. (1999) "An Essential Role for Interleukin 10 in the Function of Regulatory T Cells that Inhibit Intestinal Inflammation." *J. Exp. Med.*, vol. 190(7):995-1003.
Bamford (1999) "Chronic Gastrointestinal Inflammation." *FEMS Immunology and Medical Microbiology*, vol. 24:161-168.
Bhan et al. (1999) "Colitis in Transgenic and Knockout Animals as Models of Human Inflammatory Bowel Disease." *Immunological Reviews*, vol. 169:195-207.
Blumberg et al. (1999) "Animal models of mucosal inflammation and their relation to human inflammatory bowel disease." *Current Opinions in Immunology*, vol. 11:648-656.
Blumberg et al. (2001) "Prospects for research in Inflammatory Bowel Disease." *JAMA*, vol. 285(5):643-647.
Dieleman et al. (1998) "Chronic experimental colitis induced by dextran sulphate sodium (DSS) is characterized by Th1 and Th2 cytokines." *Clin. Exp. Immunol.*, vol. 114:385-391.
Dohi et al. (1999) "Hapten-induced Colitis is Associated with Colonic Patch Hypertrophy and T Helper Cell 2-Type Responses." *J. Exp. Med.*, vol. 189(8):1169-1179.
Hyams (2000) "Coricosteroids in the treatment of gastrointestinal disease." *Current Opinion in Pediatrics*, vol. 12:451-455.
Iijima et al. (1999) "Alteration of Interleukin 4 Production Results in the Inhibition of T Helper Type 2 Cell-dominated Inflammatory Bowel Disease in T Cell Receptor α Chain-deficient Mice." *J. Exp. Med.*, vol. 190(5):607-615.
MacDonald (1997) "Cytokine gene delted mice in the study of gastrointestinal inflammation." *Eur. J. Gastroenterol. & Hepatol.*, vol. 9:1051-1055.
Mayer et al. (2000) Current concept of IBD: Etiology and Pathogenesis. In "Inflammatory Bowel Disease." 5th Edition, Kirsner JB editor, W.B. Saunders Company, pp. 280-296.
Mikula (1999) "Anti-TNFα: New Therapy for Crohn's Disease." *Gastroenterol Nurs.*, vol. 22(6):245-8.
Nagura et al. (2001) "The Immuno-Inflammatory Mechanism for Tissue Injury in Inflammatory Bowel Disease and Helicobacter pylori-Infected Chronic Active Gastritis." *Digesion*, vol. 63(1):12-21.
Neurath et al. (1997) "Predominant pathogenic role of tumor necrosis factor in experimental colitis in mice." *Eur. J. Immunol.*, vol. 27:1743-1750.

(Continued)

*Primary Examiner*—Mark Navarro
*Assistant Examiner*—Nina A Archie
(74) *Attorney, Agent, or Firm*—Paula A. Borden; Bozicevic, Field & Francis LLP

(57) ABSTRACT

The invention provides a method for ameliorating gastrointestinal inflammation, particularly chronic gastrointestinal inflammation such as inflammatory bowel disease (IBD), in a subject. In one embodiment, the method comprises administering an immunomodulatory nucleic acid to a subject suffering from or susceptible to gastrointestinal inflammation.

46 Claims, 8 Drawing Sheets

OTHER PUBLICATIONS

Neurath et al. (2000) "TNBS-Colitis." *Int. Rev. Immunol.*, vol. 19:51-6.

Nishimura et al. (1999) "Distinct Role of Antigen-specific T Helper Type 1 (Th1) and Th2 Cells in Tumor Eradication in vivo." *J. Exp. Med.*, vol. 190(5):617-627.

Papadakis et al. (2000) "Role of Cytokines in the Pathogenesis of Inflammatory Bowel Disease." *Annu. Rev. Med.*, vol. 51:289-298.

Podolsky (1999) "Mucosal Immunity and Inflammation V. Innate mechanisms of mucosal defense and repair: the best offense is a good defense." *Am. J. Physiol.*, vol. 277:G495-499.

Pohl et al. (2000) "Chronic Inflammatory Bowel Disease and Cancer." *Hepato-Gastroenterology*, vol. 47:57-70.

Roman et al. (1997) "Immunostimulatory DNA sequences function as T helper-1-promoting adjuvants." *Nature Medicine*, vol. 3(8):849-854.

Sartor (1997) "Pathogenesis and Immune Mechanisms of Chronic Inflammatory Bowel Diseases." *The Amer. Journal of Gastroenterology*, vol. 92(12):5S-11S.

Schappi et al. (2001) "Colitis in chronic granulomatous disease." *Arch. Disc. Child.*, vol. 84:147-151.

Walker-Smith (2000) "Chronic inflammatory bowel disease in children: a complex problem in management." *Postgrad Med. J.*, vol. 76(898):469-472.

Janeway "Basic Concepts in Immunology" 5TH Edition, c 2000, *Immuno Biology*.

Janeway et al., "Manipulation of the Immune Response" 4TH Edition (1999), *Immuno Biology*, pp. 536-539.

Nagler-Anderson et al., "Suppression of type II collagen-induced arthritis by intragastric administration of soluble type II collagen", Prac. Natl. Acad. Sci. (1986), 83:7743-7446.

Desvignes et al., "Oral Administration of Hapten Inhibits In Vivo Induction of Specific Cytotoxic CD8 T Cells Mediating tissue Inflammation: A Role for Regulatory CD4 T Cells" The Journal of Immunology (2000) 2515-2522.

Raghavan et al., "Orally Administered CpG Oligodeooxynucleotide Induces Production of CXC and CC Chemokines in the Gastric Mucosa and Suppresses Bacterial Colonization in a Mouse Model of Helicobacter Pylori Infection" Infection and Immunity (2003) 71:7014-7022.

Kuolee et al., "Mouse Model of Oral Infection with Virulent Type A *Francisella tularensis*" Infection and Immunity (2007) 75:1651-1660.

* cited by examiner

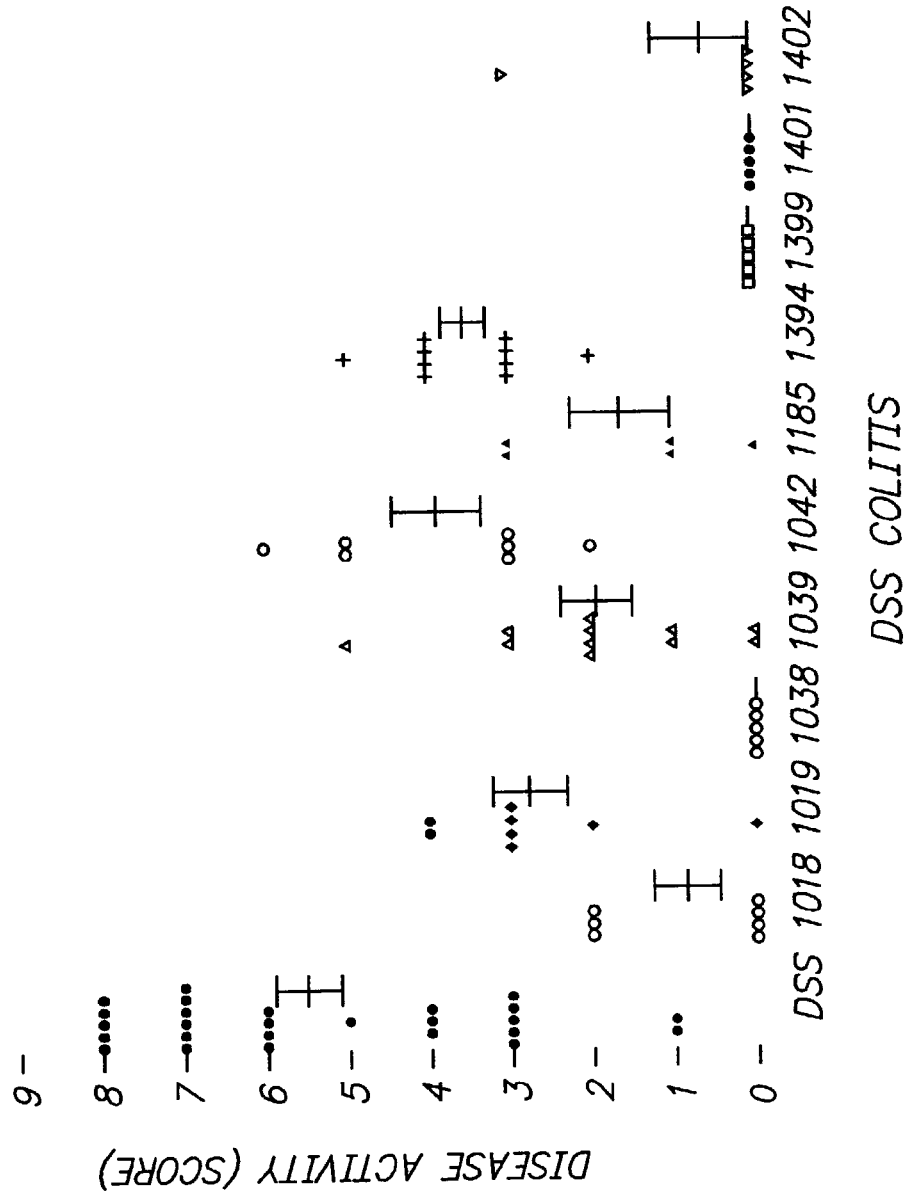

Effect of ISS (sc) on DSS induced Colitis

Effect of ISS (i.g.) on DSS induced Colitis

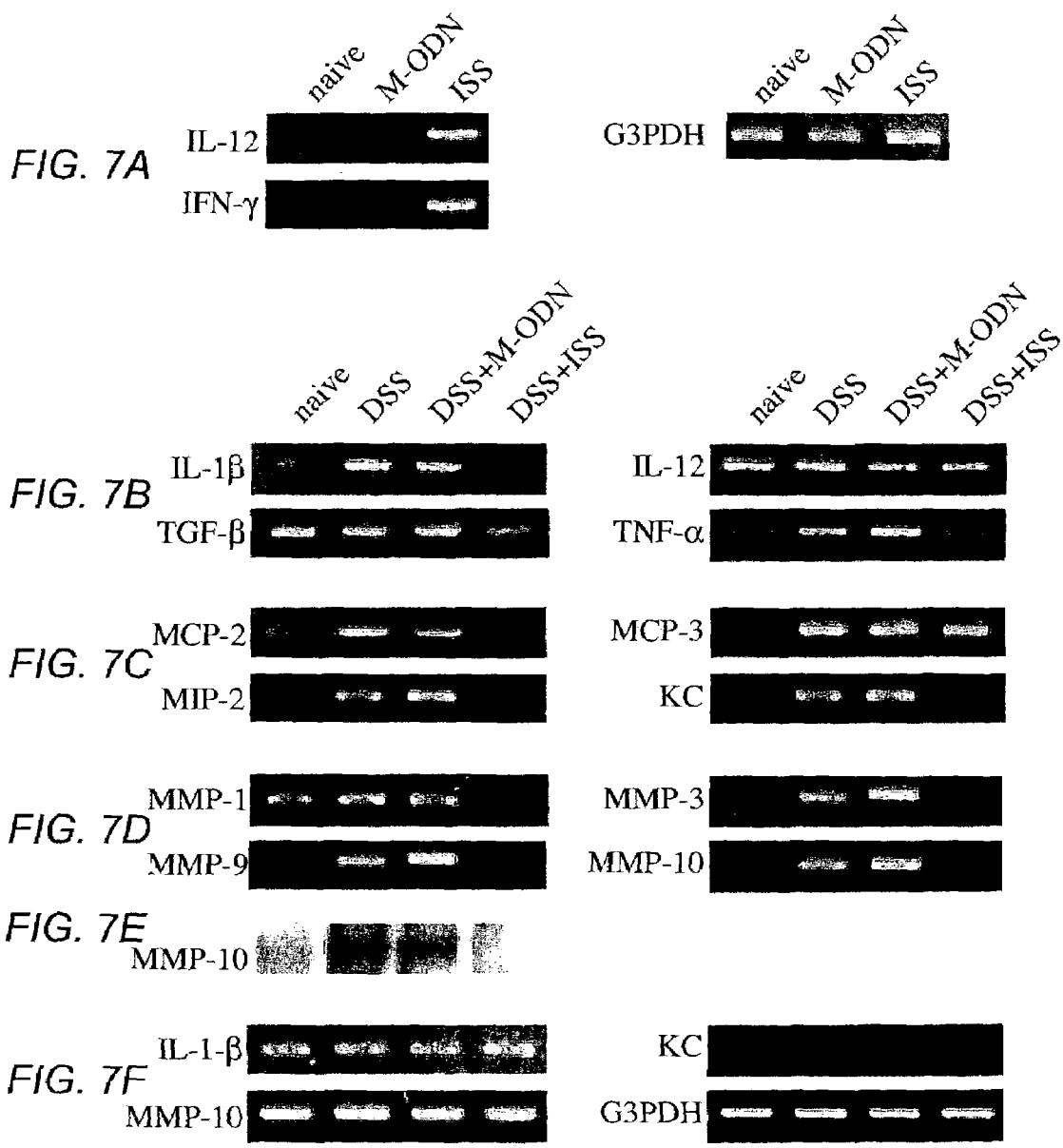

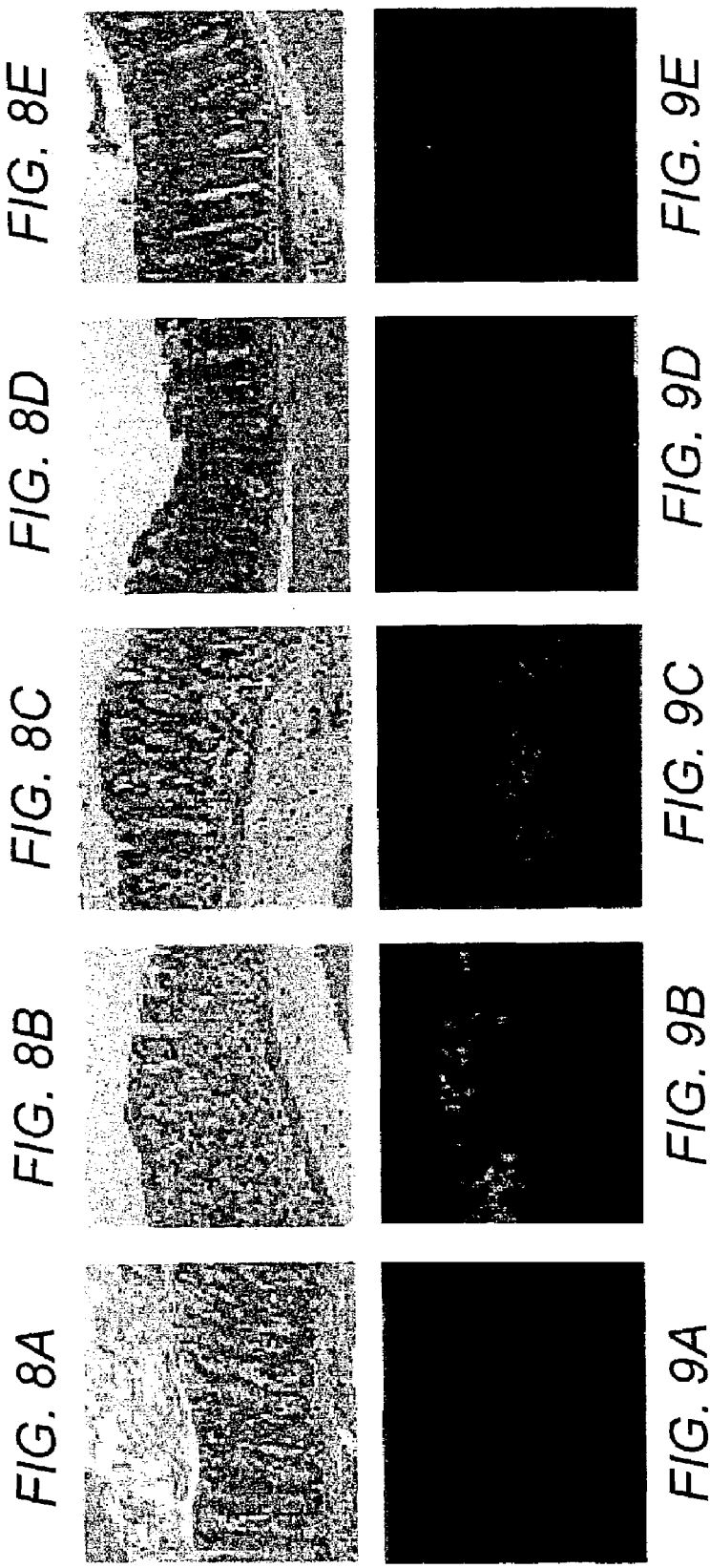

SEQUENCE LISTING

```
<160> NUMBER OF SEQ ID NOS: 39

<210> SEQ ID NO 1
<211> LENGTH: 22
<212> TYPE: DNA
<213> ORGANISM: Artificial Sequence
<220> FEATURE:
<223> OTHER INFORMATION: synthetic polynucleotide sequence
<223> OTHER INFORMATION: oligonucleotide primer
<220> FEATURE:
<223> OTHER INFORMATION: oligonucleotide primer

<400> SEQUENCE: 1
tgactgtgaa cgttcgagat ga                                              22

<210> SEQ ID NO 2
<211> LENGTH: 22
<212> TYPE: DNA
<213> ORGANISM: Artificial Sequence
<220> FEATURE:
<223> OTHER INFORMATION: synthetic polynucleotide sequence

<400> SEQUENCE: 2
```

-continued tgactgtgtt ccttagagat ga                                          22

<210> SEQ ID NO 3
<211> LENGTH: 22
<212> TYPE: DNA
<213> ORGANISM: Artificial Sequence
<220> FEATURE:
<223> OTHER INFORMATION: synthetic polynucleotide sequence

<400> SEQUENCE: 3
tgactgtgaa ccttagagat ga                                          22

<210> SEQ ID NO 4
<211> LENGTH: 22
<212> TYPE: DNA
<213> ORGANISM: Artificial Sequence
<220> FEATURE:
<223> OTHER INFORMATION: synthetic polynucleotide sequence

<400> SEQUENCE: 4
tgactgtgaa ggttcgagat ga                                          22

<210> SEQ ID NO 5
<211> LENGTH: 22
<212> TYPE: DNA
<213> ORGANISM: Artificial Sequence
<220> FEATURE:
<223> OTHER INFORMATION: synthetic polynucleotide sequence

<400> SEQUENCE: 5
tgactgtgaa cgttagagat ga                                          22

<210> SEQ ID NO 6
<211> LENGTH: 22
<212> TYPE: DNA
<213> ORGANISM: Artificial Sequence
<220> FEATURE:
<223> OTHER INFORMATION: synthetic polynucleotide sequence

<400> SEQUENCE: 6
tgactgtgaa cgttagagat ga                                          22

<210> SEQ ID NO 7
<211> LENGTH: 20
<212> TYPE: DNA
<213> ORGANISM: Artificial Sequence
<220> FEATURE:
<223> OTHER INFORMATION: synthetic polynucleotide sequence

<400> SEQUENCE: 7
tccatgacgt tcctgatgct                                             20

<210> SEQ ID NO 8
<211> LENGTH: 22
<212> TYPE: DNA
<213> ORGANISM: Artificial Sequence
<220> FEATURE:
<223> OTHER INFORMATION: synthetic polynucleotide sequence

<400> SEQUENCE: 8
tgactgtgaa tgttagagat ga                                          22

<210> SEQ ID NO 9
<211> LENGTH: 22
<212> TYPE: DNA
<213> ORGANISM: Artificial Sequence -continued

```
<220> FEATURE:
<223> OTHER INFORMATION: synthetic polynucleotide sequence

<400> SEQUENCE: 9
tgactgtggt cgttagagat ga                                              22

<210> SEQ ID NO 10
<211> LENGTH: 22
<212> TYPE: DNA
<213> ORGANISM: Artificial Sequence
<220> FEATURE:
<223> OTHER INFORMATION: synthetic polynucleotide sequence

<400> SEQUENCE: 10
tcgtcgtcgt cgtcgtcgtc gt                                              22

<210> SEQ ID NO 11
<211> LENGTH: 22
<212> TYPE: DNA
<213> ORGANISM: Artificial Sequence
<220> FEATURE:
<223> OTHER INFORMATION: synthetic polynucleotide sequence

<400> SEQUENCE: 11
tgaaacgttc gcctgtcgtt ga                                              22

<210> SEQ ID NO 12
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 12
atgagctttg tacaaggaga acca                                            24

<210> SEQ ID NO 13
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 13
ttaggaagac acagattcca tggt                                            24

<210> SEQ ID NO 14
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 14
ggtgacatga aaatcctgca gagc                                            24

<210> SEQ ID NO 15
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 15
tcagcagcga ctccttttcc gctt                                            24
```

<210> SEQ ID NO 16
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 16
gggacatcat caaaccagac c                                             21

<210> SEQ ID NO 17
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 17
gccaaccaag cagaagacag c                                             21

<210> SEQ ID NO 18
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 18
gataccaact attgcttcag ctccaca                                       27

<210> SEQ ID NO 19
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 19
tcagctgcac ttgcaggagc gcacaat                                       27

<210> SEQ ID NO 20
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 20
atcagttcta tggcccagac cctcaca                                       27

<210> SEQ ID NO 21
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 21
tcacagagca atgactccaa agtagag                                       27

<210> SEQ ID NO 22
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 22
atgaagatct acgcagtgct tctttgc                                              27

<210> SEQ ID NO 23
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 23
tcaaggctgc agaatttgag acttctg                                              27

<210> SEQ ID NO 24
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 24
atgaggatct ctgccacgct tctgtgc                                              27

<210> SEQ ID NO 25
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 25
aggctttgga gttggggttt tcatgtc                                              27

<210> SEQ ID NO 26
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 26
atggcccctc ccacctgccg gctcctc                                              27

<210> SEQ ID NO 27
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 27
aggtacgatc caggcttccc gggtgct                                              27

<210> SEQ ID NO 28
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 28
atgatcccag ccacccgctc gcttctc                                              27

<210> SEQ ID NO 29

```
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 29
ttacttgggg acaccttta gcatctt                                            27

<210> SEQ ID NO 30
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 30
aacaaatact ggaagttcaa caac                                              24

<210> SEQ ID NO 31
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 31
tcagaccttg tccagcagcg aacg                                              24

<210> SEQ ID NO 32
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 32
aaggggatcc ctgaatcacc tcag                                              24

<210> SEQ ID NO 33
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 33
tcacacccac tcttgcatag accg                                              24

<210> SEQ ID NO 34
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 34
tggtactgga agttcctgaa tcataga                                           27

<210> SEQ ID NO 35
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 35
```

```
caagggcact gcaggaggtc gtaggtc                                       27

<210> SEQ ID NO 36
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 36
gcagtccgag gaaatgaagt ccaa                                          24

<210> SEQ ID NO 37
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 37
tcagcacagc agccagctgt tgct                                          24

<210> SEQ ID NO 38
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 38
accacagtcc atgccatcac                                               20

<210> SEQ ID NO 39
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 39
tccaccaccc tgttgctgta                                               20
```

METHOD FOR TREATING INFLAMMATORY BOWEL DISEASE AND OTHER FORMS OF GASTROINTESTINAL INFLAMMATION

CROSS-REFERENCE TO RELATED APPLICATIONS

This application claims the benefit of U.S. Provisional Application Serial No. 60/184,256, filed Feb. 23, 2000, which application is incorporated herein by reference in its entirety.

STATEMENT AS TO FEDERALLY SPONSORED RESEARCH

The invention was made with the Government support under Grant No. AI40682, awarded by the National Institutes of Health. The government has certain rights in this invention.

Throughout this application various publication are referenced. The disclosures of these publications in their entireties are hereby incorporated by reference into this application in order to describe more fully state of the art to which this invention pertains.

TECHNICAL FIELD OF THE INVENTION

The invention relates to a method for ameliorating inflammation of the gastrointestinal tract, such as that associated with inflammatory bowel disease, in a subject. The method involves administering a nucleic acid comprising an immunomodulatory nucleotide sequence to the subject. The immunomodulatory sequence can be administered alone or together with an additional therapeutic agents.

BACKGROUND OF THE INVENTION

Gastrointestinal inflammation is one of the most common types of inflammatory process which affects humans (for a review, see, e.g., Bamford, FEMS Immunol Med Microbiol (1999) 24(2):161-8). Inflammatory bowel disease (IBD), a form of chronic gastrointestinal inflammation, includes a group of chronic inflammatory disorders of generally unknown etiology, e.g., ulcerative colitis (UC) and Crohn's disease (CD). Clinical and experimental evidence suggest that the pathogenesis of IBD is multifactorial involving susceptibility genes and environmental factors (Sartor Am J Gastroenterol. (1997) 92:5S-11S). The interaction of these factors with the immune system leads to intestinal inflammation and dysregulated mucosal immunity against commensal bacteria, various microbial products (e.g., LPS) or antigens (Mayer et al. Current concept of IBD: Etiology and pathogenesis. In "Inflammatory Bowel Disease" 5$^{th}$ edition 2000, Kirsner JB editor. W. B. Sanunders Company, pp 280-296; for a discussion of IBD in children see, e.g., Walker-Smith, Postgrad Med J (2000) 76(898):469-72).

Human Crohn's disease (CD) is thought to be characterized by type 1 Helper T (Th-1) response, which produce the cytokines interleukin IL-2, interferon γ, and tumor necrosis factor TNF (for a review of anti-TNFα therapy in Crohn's disease, see, e.g., Mikula Gastroenterol Nurs. (1999) 22(6): 245-8; Selby, Vet Microbiol (2000) 77(3-4):505-511). Ulcerative colitis (UC) is dominated by type 2 Helper T (Th-2) response which produce anti-inflammatory cytokines such as IL-4, IL-5 and IL-10. However, the demarcation between Th-1 and Th-2 response in CD and UC is not an "all or none" response and it seems that there is significant overlap.

Animal models of colitis have highlighted the prominent role of CD4+ T cells in the regulation of intestinal inflammation (Blumberg et al. Curr Opin Immunol (1999) 6:648-56). Cytokine imbalance, and the production of inflammatory mediators have been postulated to play an important role in the pathogenesis of both experimental colitis and IBD (Papadakis et al. Annu Rev Med (2000) 51:289-98; for a review, see, e.g., Blumberg JAMA (2001) 285(5):643-647; Nagura et al. Digestion (2001) 63 Suppl S1:12-21). In particular, dysregulated CD4+ T cell responses play a pivotal role in the pathogenesis of experimental colitis (Bhan et al. Immunol Rev (1999) 169:195-207). Indeed, Th1 cytokines (e.g., IL-12) are dominant in inflamed mucosa of CD, whereas Th2 cytokines (e.g., IL-4) are relatively common in UC. In this respect, dinitrobenzene sulphonic acid-induced colitis (DNB), which is characterized by predominating Th1 response in mice (Neurath et al. Int Rev Immunol (2000) 19:51-6) mimics CD, whereas dextran sodium sulphate (DSS) induces acute and chronic colitis with a mixed Th1/Th2-like response, features UC (Dieleman et al. Clin Exp Immunol (1998) 114:385-91). Studies using transgenic mice having deletions in a cytokine gene develop a spontaneous inflammatory bowel disease (for a review see, e.g., MacDonald, Eur J Gastroenterol Hepatol (1997) 9(11):1051-50). animals having cytokine DNB-induced colitis, which is driven by mucosal Th1 response, has been reported to be accelerated by rIL-12 and inhibited by administration of anti-IL-12 antibodies (Neurtah et al. (2000), ibid). The inflammatory process and the immune response at mucosal sites result in mucosal barrier dysfunction leading to further exposure to enteric bacteria and/or their products that perpetuate mucosal inflammation (Podolsky Am J Physiol (1999) 277:G495-9).

Immunosuppressive and anti-inflammatory agents in high maintenance doses are the principal drugs used in the therapy of chronic inflammatory gastrointestinal disorders. Anti-inflammatory drugs presently used in treatment of IBD include aminosalycilates and immunosuppressive agents such as corticosteroids, azathioprine, cyclosporine and methotrexate. Corticosteroids remain the mainstay of anti-inflammatory and immunosuppressive therapy for many gastrointestinal conditions (see, e.g., Hyams, Curr Opin Pediatr (2000);12(5): 451-5). Recently, specific anti-TNF antibodies have been used for treatment of IBD. About 20-25% of the patients with UC fail to respond to intensive and optimal medical therapy and therefore are referred to surgery for total proctocolectomy. In general, patients with CD are less responsive to medical therapy and usually do not respond to surgical treatment. Recently, anti-TNFα antibodies were introduced to treat patients with CD with reasonable efficacy, but this approach is ineffective in patients with UC. Thus, IBD is a medical problem that lacks an effective treatment.

The importance of management of gastrointestinal inflammation, particular chronic gastrointestinal inflammation, can not be underestimated, since the presence of gastrointestinal inflammation can be an early sign for risk of development of further serious conditions. For example, colorectal cancer represents the major cause for excess morbidity and mortality by malignant disease in ulcerative colitis as well as in Crohn's disease. The risk for ulcerative colitis associated colorectal cancer is increased at least 2-fold compared to the normal population. Colorectal cancer is observed in 5.5-13.5% of all patients with ulcerative colitis and 0.4-0.8% of patients with Crohn's disease. Ulcerative colitis associated colorectal cancer typically can occur in the entire colon, is often multifocal and of undifferentiated histology. Stage distribution and prognosis of ulcerative colitis associated colorectal cancer appears to be similar to that of sporadic colorectal cancer with an overall survival of about 40% (15-65%) after 5 years with tumor stage at diagnosis being the most important predictive parameter for survival (for a review see, e.g., Pohl et al. Hepatogastroenterology (2000) 47(31):57-70).

There is a need in the field for effective methods of treating gastrointestinal inflammation, particularly chronic gastrointestinal inflammation such as IBD. The present invention addresses this need.

SUMMARY OF THE INVENTION

The invention provides a method for ameliorating gastrointestinal inflammation, particularly chronic gastrointestinal inflammation such as inflammatory bowel disease (IBD), in a subject. In one embodiment, the method comprises administering an immunomodulatory nucleic acid to a subject suffering from or susceptible to gastrointestinal inflammation.

The immunomodulatory nucleic acid can be administered via gastroenteral or parenteral routes. Examples of gastroenteral routes include, but are not limited to, oral, gastric or rectal administration. Examples of parenteral routes include, but are not limited to, intradermal, intramuscular, subcutaneous or intravenous administration. The immunomodulatory nucleic acid can be administered alone or together with additional therapeutic agents.

In exemplary embodiments, the immunomodulatory nucleic acid comprises a non-coding oligonucleotide sequence that may include at least one unmethylated CpG motif. Examples of an immunomodulatory nucleic acid include, but are not limited to, sequences comprising 5'-rrcgyy-3', such as AACGTT, AGCGTT, GACGTT, GGCGTT, AACGTC, and AGCGTC, 5'-rycgyy-3' such as GTCGTT, 5'-rrcgyycg-3', 5'-rycgyycg-3' or 5'-(TCG)$_n$-3'. An immunomodulatory nucleic acid of particular interest is one comprising the sequence 5'-AACGTTCG-3'. In one exemplary embodiment, the immunomodulatory nucleic acid is plasmid DNA or bacterial genomic DNA.

BRIEF DESCRIPTION OF THE FIGURES

FIG. 2 is a graph showing the effect of various immunomodulatory polynucleotide upon disease activity index in DSS-induced colitis.

FIGS. 7A-7F are exemplary results from RT-PCR and Western blot analysis of colonic tissues of naïve (no DSS, no polynucleotide), DSS-treated (DSS), DSS and control M-ODN treated (DSS+M-ODN), and DSS-treated, immunomodulatory polynucleotide-treated (DSS+ISS) mice.

FIGS. 8A-8E are photographs of H&E stained sections of colon taken from control, DSS-treated, or DSS-treated and immunomodulatory polynucleotide-treated mice. FIG. 8A, control (no DSS, no polynucleotide); FIG. 8B, DSS alone; FIG. 8C, DSS and subcutaneous control M-ODN; FIG. 8D, DSS and subcutaneous immunomodulatory polynucleotide; and FIG. 8E, DSS and intragastric immunomodulatory polynucleotide.

FIGS. 9A-9E are photographs of TUNEL assays of colon sections taken from control, DSS-treated, or DSS-treated and immunomodulatory polynucleotide-treated mice. FIG. 9A, control (no DSS, no polynucleotide); FIG. 9B, DSS alone; FIG. 9C, DSS and subcutaneous control M-ODN; FIG. 9D, DSS and subcutaneous immunomodulatory polynucleotide; and FIG. 9E, DSS and intragastric immunomodulatory polynucleotide.

DETAILED DESCRIPTION OF THE INVENTION

Figure 1A:
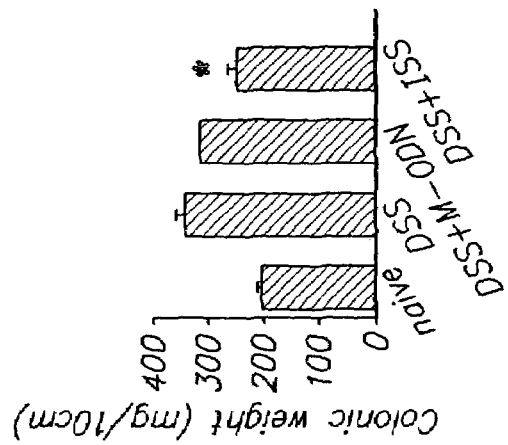
FIGS. 1A-1D are graphs showing the effects of a single subcutaneous administration of immunomodulatory polynucleotide or control M-ODN (10 μg/mouse), administered 2 hrs prior to DSS challenge, in an animal model of colitis. Disease activity index (DAI) (FIG. 1A), change in body weight (FIG. 1B) colonic weight (FIG. 1C) and colonic MPO activity (FIG. 1D) were reduced in immunomodulatory polynucleotide-treated animals. Data represent one experiment out of three.
Figure 1B:
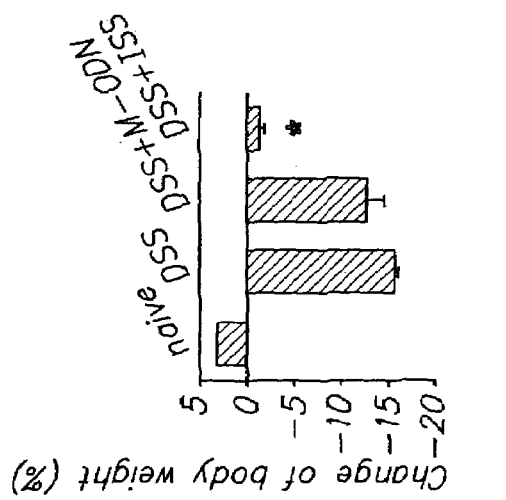
Figure 1C:
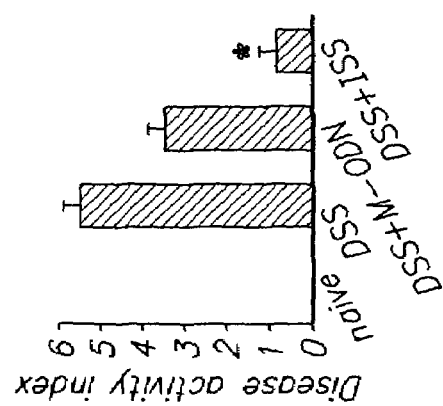

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of such cells and reference to "the polynucleotide" includes reference to one or more polynucleotides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "immunomodulatory nucleic acid molecule," "immunomodulatory sequence," "immunostimulatory sequence," "ISS," "ISS-PN," and "ISS-ODN," used interchangeably herein, refer to a polynucleotide that comprises at least one immunomodulatory nucleic acid moiety, e.g., a sequence comprising an immunomodulatory consensus sequence 5'-rrcgyy-3'. The term "immunomodulatory," as used herein in reference to a nucleic acid molecule, refers to the ability of a nucleic acid molecule to modulate an immune response in a vertebrate host. In general the immunomodulatory sequence moiety is a single-or double-stranded DNA or RNA oligonucleotide having at least six nucleotide bases that may comprise, or consist of, a modified oligonucleotide or a sequence of modified nucleosides. Preferably, the immunomodulatory moieties comprise, or may be flanked by, a CG containing nucleotide sequence or a p(IC) nucleotide sequence, which may be palindromic. Immunomodulatory sequences include any immunomodulatory sequence-enriched DNA, such as microbial or plasmid DNA: It should be noted that these sequences were originally identified by their activity in stimulating an immune response, and hence are referred to as an "immunostimulatory sequence" or "ISS". However, this designation is to be viewed as a reference that results from the history of these polynucleotides in the art, and is not meant to suggest that the sequences have activity only in stimulation of immune responses, particular in view of the activity of these sequences in both suppressing and enhancing various aspects of immune responses (e.g., enhancing Th1-based immune responses while decreasing Th2-based immune responses)

The terms "oligonucleotide," "polynucleotide," "sequence," and "nucleic acid molecule", used interchangeably herein, refer to polymeric forms of nucleotides of any length, either ribonucleotides or deoxyribonucleotides. Thus, this term includes, but is not limited to, single-, double-, or multi-stranded DNA or RNA, genomic bacterial DNA, plasmid DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites, and/or phosphorothioates, and thus can be an oligodeoxynucleoside phosphoramidate or a mixed phosphoramidate-phosphodiester oligomer. Peyrottes et al. (1996) *Nucl. Acids Res.* 24:1841-1848; Chaturvedi et al. (1996) *Nucl. Acids Res.* 24:2318-2323. The polynucleotide may comprise one or more L-nucleosides. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be modified to comprise N3'-P5' (NP) phosphoramidate, morpholino phosphorociamidate (MF), locked nucleic acid (LNA), 2'-O-methoxyethyl (MOE), or 2'-fluoro, arabinonucleic acid (FANA), which can enhance the resistance of the polynucleotide to nuclease degradation (see, e.g., Faria et al. (2001) *Nature Biotechnol.* 19:40-44; Toulme (2001) *Nature Biotechnol.* 19:17-18). A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Immunomodulatory nucleic acid molecules can be provided in various formulations, e.g., in association with liposomes, microencapsulated, etc., as described in more detail herein.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, preferably 75% free, and most preferably 90% free from other components with which it is naturally associated.

"Gastrointestinal inflammation" as used herein refers to inflammation of a mucosal layer of the gastrointestinal tract, and encompasses acute and chronic inflammatory conditions. Acute inflammation is generally characterized by a short time of onset and infiltration or influx of neutrophils. Chronic inflammation is generally characterized by a relatively longer period of onset and infiltration or influx of mononuclear cells. Chronic inflammation can also typically characterized by periods of spontaneous remission and spontaneous occurrence. "Mucosal layer of the gastrointestinal tract" is meant to include mucosa of the bowel (including the small intestine and large intestine), rectum, stomach (gastric) lining, oral cavity, and the like.

"Chronic gastrointestinal inflammation" refers to inflammation of the mucosal of the gastrointestinal tract that is characterized by a relatively longer period of onset, is long-lasting (e.g., from several days, weeks, months, or years and up to the life of the subject), and is associated with infiltration or influx of mononuclear cells and can be further associated with periods of spontaneous remission and spontaneous occurrence. Thus, subjects with chronic gastrointestinal inflammation may be expected to require a long period of supervision, observation, or care. "Chronic gastrointestinal inflammatory conditions" (also referred to as "chronic gastrointestinal inflammatory diseases") having such chronic inflammation include, but are not necessarily limited to, inflammatory bowel disease (IBD), colitis induced by environmental insults (e.g., gastrointestinal inflammation (e.g., colitis) caused by or associated with (e.g., as a side effect) a therapeutic regimen, such as administration of chemotherapy, radiation therapy, and the like), colitis in conditions such as chronic granulomatous disease (Schappi et al. Arch Dis Child. February 2001;84(2):147-151), celiac disease, celiac sprue (a heritable disease in which the intestinal lining is inflamed in response to the ingestion of a protein known as gluten), food allergies, gastritis, infectious gastritis or enterocolitis (e.g., Helicobacter pylori-infected chronic active gastritis) and other forms of gastrointestinal inflammation caused by an infectious agent, and other like conditions.

As used herein, "inflammatory bowel disease" or "IBD" refers to any of a variety of diseases characterized by inflammation of all or part of the intestines. Examples of inflammatory bowel disease include, but are not limited to, Crohn's disease and ulcerative colitis. Reference to IBD throughout the specification is often referred to in the specification as exemplary of gastrointestinal inflammatory conditions, and is not meant to be limiting.

As used herein, "subject" or "individual" or "patient" refers to any subject for whom or which therapy is desired, and generally refers to the recipient of the therapy to be practiced according to the invention. The subject can be any vertebrate, but will preferably be a mammal. If a mammal, the subject will preferably be a human, but may also be a domestic livestock, laboratory subject or pet animal.

"Treatment" or "treating" as used herein means any therapeutic intervention in a subject, usually a mammalian subject, generally a human subject, including: (i) prevention, that is, causing the clinical symptoms not to develop, e.g., preventing progression to a harmful state; (ii) inhibition, that is, arresting the development or further development of clinical symptoms, e.g., mitigating or completely inhibiting active (ongoing) inflammation so as to decrease inflammation, which decrease can include substantially complete elimination of inflammation; and/or (iii) relief, that is, causing the regression of clinical symptoms, e.g., causing relief from diarrhea, rectal bleeding and weight loss, reduction in colon weight, reduction in colon lesions, reduction of strictures, reduction of fistulae, and/or reduction colonic inflammation.

The term "effective amount" or "therapeutically effective amount" means a dosage sufficient to provide for treatment for the disease state being treated or to otherwise provide the desired effect (e.g., reduction of inflammation). The precise dosage will vary according to a variety of factors such as subject-dependent variables (e.g., age, immune system health, etc.), the disease (e.g., the type of gastrointestinal inflammation), and the treatment being effected. In the case of treatment of gastrointestinal inflammation, an "effective amount" is that amount sufficient to substantially improve the likelihood of treating the inflammation or other symptom of a gastrointestinal inflammatory disease such as IBD.

As used herein, "pharmaceutically acceptable carrier" includes any material which, when combined with an active ingredient of a composition, allows the ingredient to retain biological activity and without causing disruptive reactions with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, Chapter 43, 14th Ed., Mack Publishing Col, Easton Pa. 18042, USA).

Overview

The present invention is based on the discovery that enteral and parenteral administration of immunomodulatory polynucleotide sequences (referred to herein for convenience's sake as ISS) to a subject are effective in reducing symptoms of an inflammatory condition of the gastrointestinal tract, such as that of inflammatory bowel disease (IBD). The invention provides a new and potent therapeutic advantage that is effective across species in a variety of animal models of chronic and/or acute gastrointestinal inflammation, particularly in animal models of IBD, which animal models are regarded in the field as models of disease in humans. Immunomodulatory nucleic acid in treatment of gastrointestinal inflammation shown herein to reduce disease activity, e.g., diarrhea, rectal bleeding and weight loss, to reduce colon weight and colon lesions, as well as to reduce colonic inflammation, as measured by, for example, anti-neutrophil cytoplasmic antibodies (ANCA), colonic myclo-peroxidase activity, or other conventional indicator of gastrointestinal inflammation, and such indicators can be sued to monitor immunomodulatory nucleic acid-based therapy as described herein. This discovery offers an attractive new treatment strategy for the large number of patients suffering from gastrointestinal inflammation, particularly chronic gastrointestinal inflammation, such as those patients suffering from IBD, particularly those patients for whom no satisfactory and effective treatment is currently available.

Nucleic Acid Molecules Comprising Immunomodulatory Nucleic Acid Molecule

Nucleic acid molecules comprising an immunomodulatory nucleic acid molecule which are suitable for use in the methods of the invention include an oligonucleotide, which can be a part of a larger nucleotide construct such as a plasmid and larger structures such as genomic bacterial DNA. The term "polynucleotide" therefore includes oligonucleotides, modified oligonucleotides and oligonucleosides, alone or as part of a larger construct. The polynucleotide can be single-stranded DNA (ssDNA), double-stranded DNA (dsDNA), single-stranded RNA (ssRNA) or double-stranded RNA (dsRNA). The polynucleotide portion can be linearly or circularly configured, or the oligonucleotide portion can contain both linear and circular segments. Immunomodulatory nucleic acid molecules also encompasses crude, detoxified bacterial (e.g., mycobacterial) RNA or DNA, as well as ISS-enriched plasmids. "ISS-enriched plasmid" as used herein is meant to refer to a linear or circular plasmid that comprises or is engineered to comprise a greater number of CpG motifs than normally found in mammalian DNA. Exemplary ISS-enriched plasmids are described in, for example, Roman et al. (1997) *Nat Med.* 3(8):849-54. Modifications of polynucleotides include, but are not limited to, modifications of the 3'OH or 5'OH group, modifications of the nucleotide base, modifications of the sugar component, and modifications of the phosphate group. Bacterial DNA can also be modified as described herein for use in the invention.

The immunomodulatory nucleic acid molecule can comprise ribonucleotides (containing ribose as the only or principal sugar component), deoxyribonucleotides (containing deoxyribose as the principal sugar component), or in accordance with the established state-of-the-art, modified sugars or sugar analogs may be incorporated in the oligonucleotide of the present invention. Examples of a sugar moiety that can be used include, in addition to ribose and deoxyribose, pentose, deoxypentose, hexose, deoxyhexose, glucose, arabinose, xylose, lyxose, and a sugar "analog" cyclopentyl group. The sugar may be in pyranosyl or in a furanosyl form. In the modified oligonucleotides of the present invention, the sugar moiety is preferably the furanoside of ribose, deoxyribose, arabinose or 2'-O-methylribose, and the sugar may be attached to the respective heterocyclic bases either in I or J anomeric configuration.

An immunomodulatory nucleic acid molecule may comprise at least one nucleoside comprising an L-sugar. The L-sugar may be deoxyribose, ribose, pentose, deoxypentose, hexose, deoxyhexose, glucose, galactose, arabinose, xylose, lyxose, or a sugar "analog" cyclopentyl group. The L-sugar may be in pyranosyl or furanosyl form.

The phosphorous derivative (or modified phosphate group) that can be attached to the sugar or sugar analog moiety in the modified oligonucleotides of the present invention can be a monophosphate, diphosphate, triphosphate, alkylphosphate, alkanephosphate, phosphorothioate, phosphorodithioate or the like. The heterocyclic bases, or nucleic acid bases that are incorporated in the oligonucleotide base of the ISS can be the naturally occurring principal purine and pyrimidine bases, (namely uracil or thymine, cytosine, adenine and guanine, as mentioned above), as well as naturally occurring and synthetic modifications of said principal bases. Those skilled in the art will recognize that a large number of "synthetic" non-natural nucleosides comprising various heterocyclic bases and various sugar moieties (and sugar analogs) are available, and that the immunomodulatory nucleic acid molecule can include one or several heterocyclic bases other than the principal five base components of naturally occurring nucleic acids. Preferably, however, the heterocyclic base in the ISS is selected from uracil-5-yl, cytosin-5-yl, adenin-7-yl, adenin-8-yl, guanin-7-yl, guanin-8-yl, 4-aminopyrrolo [2,3-d] pyrimidin-5-yl, 2-amino-4-oxopyrolo [2,3-d] pyrimidin-5-yl, 2-amino-4-oxopyrrolo [2,3-d] pyrimidin-3-yl groups, where the purines are attached to the sugar moiety of the oligonucleotides via the 9-position, the pyrimidines via the 1-position, the pyrrolopyrimidines via the 7-position and the pyrazolopyrimidines via the 1-position.

Structurally, the root oligonucleotide of the immunomodulatory nucleic acid molecule is a non-coding sequence that can include at least one unmethylated CpG motif. The relative position of any CpG sequence in ISS with immunomodulatory activity in certain mammalian species (e.g., rodents) is 5'-CG-3' (i.e., the C is in the 5' position with respect to the G in the 3' position).

Immunomodulatory nucleic acid molecules generally do not provide for, nor is there any requirement that they provide for, expression of any amino acid sequence encoded by the polynucleotide, and thus the sequence of a immunomodulatory nucleic acid molecule may be, and generally is, non-coding. Immunomodulatory nucleic acid molecules may comprise a linear double or single-stranded molecule, a circular molecule, or can comprise both linear and circular segments. Immunomodulatory nucleic acid molecules may be single-stranded, or may be completely or partially double-stranded.

In some embodiments, an immunomodulatory nucleic acid molecule is an oligonucleotide, e.g., has a sequence of from about 6 to about 200, from about 10 to about 100, from about 12 to about 50, or from about 15 to about 25, nucleotides in length.

Exemplary consensus CpG motifs of immunomodulatory nucleic acid molecules useful in the invention include, but are not necessarily limited to:

5'-Purine-Purine-[C]-[G]-Pyrimidine-Pyrimidine-3', in which the immunomodulatory nucleic acid molecule comprises a CpG motif flanked by at least two purine nucleotides (e.g., GG, GA, AG, AA, II, etc.,) and at least two pyrimidine nucleotides (CC, TT, CT, TC, UW, etc.);

5'-Purine-TCG-Pyrimidine-Pyrimidine-3';

5'-[TCG]$_n$-3', where n is any integer that is 1 or greater, e.g., to provide a oly-TCG immunomodulatory nucleic acid molecule (e.g., where n=3, the polynucleotide comprises the sequence 5'-TCGTCGTCG-3');

5'-Purine-Purine-CG-Pyrimidine-Pyrimidine-CG-3'; and

5'-Purine-TCG-Pyrimidine-Pyrimidine-CG-3'

Exemplary DNA-based immunomodulatory nucleic acid molecules useful in the invention include, but are not necessarily limited to, polynucleotides comprising the following nucleotide sequences:

AACGCC, AACGCT, ACGTC, AACGTT;
AGCGCC, AGCGCT, AGCGTC, AGCGTT;
GACGCC, GACGCT, GACGTC, GACGTT;
GGCGCC, GGCGCT, GGCGTC, GGCGTT;
ATCGCC, ATCGCT, ATCGTC, ATCGTT;
GTCGCC, GTCGCT, GTCGTC, GTCGTT; and
TCGTCG, and TCGTCGTCG.

Octameric sequences are generally the above-mentioned hexameric sequences, with an additional 3'CG. Exemplary DNA-based immunomodulatory nucleic acid molecules useful in the invention include, but are not necessarily limited to, polynucleotides comprising the following octameric nucleotide sequences:

```
AACGCCCG, AACGCTCG, AACGTCCG, AACGTTCG;

AGCGCCCG, AGCGCTCG, AGCGTCCG, AGCGTTCG;

GACGCCCG, GACGCTCG, GACGTCCG, GACGTTCG;

GGCGCCCG, GGCGCTCG, GGCGTCCG, GGCGTTCG;

ATCGCCCG, ATCGCTCG, ATCGTCCG, ATCGTTCG;

GTCGCCCG, GTCGCTCG, GTCGTCCG, and GTCGTTCG.
```

Immunomodulatory nucleic acid molecules useful in the invention can comprise one or more of any of the above CpG motifs. For example, immunomodulatory nucleic acid molecules useful in the invention can comprise a single instance or multiple instances (e.g., 2, 3, 5 or more) of the same CpG motif. Alternatively, the immunomodulatory nucleic acid molecules can comprises multiple CpG motifs (e.g., 2, 3, 5 or more) where at least two of the multiple CpG motifs have different consensus sequences, or where all CpG motifs in the immunomodulatory nucleic acid molecules have different consensus sequences.

A non-limiting example of an immunomodulatory nucleic acid molecule is one with the sequence 5'-TGACTGT-GAACGTTCGAGATGA-3' (SEQ ID NO: 1). An example of a control nucleic acid molecule is one having the sequence 5'-TGACTGTGTTCCTTAGAGATGA-3' (SEQ ID NO: 2), which differs from SEQ ID NO: 1 at the nucleotide indicated in lower case type.

Immunomodulatory nucleic acid molecules useful in the invention may or may not include palindromic regions. If present, a palindrome may extend only to a CpG motif, if present, in the core hexamer or octamer sequence, or may encompass more of the hexamer or octamer sequence as well as flanking nucleotide sequences.

The core hexamer structure of the foregoing immunomodulatory nucleic acid molecules can be flanked upstream and/or downstream by any number or composition of nucleotides or nucleosides. However, immunomodulatory nucleic acid are generally at least 6 bases in length, and preferably are between 6 and 200 bases in length, to enhance uptake of the immunomodulatory nucleic acid molecule into target tissues.

In particular, immunomodulatory nucleic acid molecules useful in the invention include those that have hexameric nucleotide sequences having "CpG" motifs. Although DNA sequences are generally preferred, RNA immunomodulatory nucleic acid molecules can be used, with inosine and/or uracil substitutions for nucleotides in the hexamer sequences.

Modifications

Immunomodulatory nucleic acid molecules can be modified in a variety of ways. For example, the immunomodulatory nucleic acid molecules can comprise backbone phosphate group modifications (e.g., methylphosphonate, phosphorothioate, phosphoroamidate and phosphorodithioate internucleotide linkages), which modifications can, for example, enhance stability of the immunomodulatory nucleic acid molecule in vivo, making them particularly useful in therapeutic applications. A particularly useful phosphate group modification is the conversion to the phosphorothioate or phosphorodithioate forms of an immunomodulatory nucleic acid molecule. Phosphorothioates and phosphorodithioates are more resistant to degradation in vivo than their unmodified oligonucleotide counterparts, increasing the half-lives of the immunomodulatory nucleic acid molecules and making them more available to the subject being treated.

Other modified immunomodulatory nucleic acid molecules encompassed by the present invention include immunomodulatory nucleic acid molecules having modifications at the 5' end, the 3' end, or both the 5' and 3' ends. For example, the 5' and/or 3' end can be covalently or non-covalently conjugated to a molecule (either nucleic acid, non-nucleic acid, or both) to, for example, increase the bio-availability of the immunomodulatory nucleic acid molecules, increase the efficiency of uptake where desirable, facilitate delivery to cells of interest, and the like. Exemplary molecules for conjugation to the immunomodulatory nucleic acid molecules include, but are not necessarily limited to, cholesterol, phospholipids, fatty acids, sterols, oligosaccharides, polypeptides (e.g., immunoglobulins), peptides, antigens (e.g., peptides, small molecules, etc.), linear or circular nucleic acid molecules (e.g., a plasmid), and the like. Additional immunomodulatory nucleic acid conjugates, and methods for making same, are known in the art and described in, for example, WO 98/16427 and WO 98/55495. Thus, the term "immunomodulatory nucleic acid molecule" includes conjugates comprising an immunomodulatory nucleic acid molecule.

Preparation of Immunomodulatory Nucleic Acid Molecules

Immunomodulatory nucleic acid molecules can be synthesized using techniques and nucleic acid synthesis equipment well known in the art (see, e.g., Ausubel et al. Current Protocols in Molecular Biology, (Wiley Intersicence, 1989); Maniatis et al. Molecular Cloning: A Laboratory Manual (Cold Spring Harbor Laboratories, New York, 1982); and U.S. Pat. Nos. 4,458,066; and 4,650,675. Individual polynucleotide fragments can be ligated with a ligase such as T4 DNA or RNA ligase as described in, e.g., U.S. Pat. No. 5,124,246. Oligonucleotide degradation can be accomplished through exposure to a nuclease, see, e.g., U.S. Pat. No. 4,650, 675. As noted above, since the immunomodulatory nucleic acid molecules need not provide for expression of any encoded amino acid sequence, the invention does not require that the immunomodulatory nucleic acid molecules be operably linked to a promoter or otherwise provide for expression of a coding sequence.

Alternatively, immunomodulatory nucleic acid molecules can be purified from E. coli or Lactobacillus, isolated from microbial species (e.g., mycobacteria) using techniques well known in the art such as purification of genomic DNA, nucleic acid hybridization, amplification (e.g., by PCR), and the like. Isolated immunomodulatory nucleic acid molecules can be purified to a substantially pure state, e.g., free of endogenous contaminants, e.g., lipopolysaccharides. Immunomodulatory nucleic acid molecules isolated as part of a larger polynucleotide can be reduced to the desired length by techniques well known in the art, such as endonuclease digestion. Other techniques suitable for isolation, purification, and production of polynucleotides to obtain ISS will be readily apparent to the ordinarily skilled artisan in the relevant field.

Circular immunomodulatory nucleic acid molecules can also be synthesized through recombinant methods or chemically synthesized. Where circular immunomodulatory nucleic acid molecules are obtained through isolation or recombinant methods, the immunomodulatory nucleic acid molecule can be provided as a plasmid. Chemical synthesis of smaller circular oligonucleotides can be performed using methods known in the art (see, e.g., Gao et al. (1995) Nucl. Acids. Res. 23:2025-9; Wang et al., (1994) Nucl. Acids Res. 22:2326-33).

Where the immunomodulatory nucleic acid molecule comprises a modified oligonucleotide, the modified oligonucleotides can be synthesized using standard chemical techniques. For example, solid-support based construction of methylphosphonates has been described in Agrawal et al. Tet. Lett. 28:3539-42. Synthesis of other phosphorous-based modified oligonucleotides, such as phosphotriesters (see, e.g., Miller et al. (1971) J. Am Chem Soc. 93:6657-65), phosphoramidates (e.g., Jager et al. (1988) Biochem. 27:7237-46), and phosphorodithioates (e.g., U.S. Pat. No. 5,453,496) is known in the art. Other non-phosphorous-based modified oligonucleotides can also be used (e.g., Stirchak et al. (1989) Nucl. Acids. Res. 17:6129-41).

Preparation of base-modified nucleosides, and the synthesis of modified oligonucleotides using such base-modified nucleosides as precursors is well known in the art, see, e.g., U.S. Pat. Nos. 4,910,300; 4,948,882; and 5,093,232. These base-modified nucleosides have been designed so that they can be incorporated by chemical synthesis into either terminal or internal positions of an oligonucleotide. Nucleosides modified in their sugar moiety have also been described (see, e.g., U.S. Pat. Nos. 4,849,513; 5,015,733; 5,118,800; and 5,118,802).

Techniques for making phosphate group modifications to oligonucleotides are known in the art. Briefly, an intermediate phosphate triester for the target oligonucleotide product is prepared and oxidized to the naturally-occurring phosphate triester with aqueous iodine or other agents, such as anhydrous amines. The resulting oligonucleotide phosphoramidates can be treated with sulfur to yield phosphorothioates. The same general technique (without the sulfur treatment step) can be used to produced methylphosphoamidites from methylphosphonates. Techniques for phosphate group modification are well known and are described in, for example, U.S. Pat. Nos. 4,425,732; 4,458,066; 5,218,103; and 5,453, 496.

Identification of Immunomodulatory Acid Molecules

Confirmation that a particular compound has the properties of an immunomodulatory nucleic acid molecule useful in the invention can be obtained by evaluating whether the immunomodulatory nucleic acid molecule elicits the appropriate cytokine secretion patterns, e.g., a cytokine secretion pattern associated with a type-1 immune response; decreases inflammation associated with gastrointestinal inflammation (e.g., in an animal model), and the like.

In general, helper T (Th) cells are divided into broad groups based on their specific profiles of cytokine production: Th1, Th2, and Th0. "Th1" cells are T lymphocytes that release predominantly the cytokines IL-2 and IFN-γ, which cytokines in turn promote T cell proliferation, facilitate macrophage activation, and enhance the cytolytic activity of natural killer (NK) cells and antigen-specific cytotoxic T cells (CTL). In contrast, the cytokines predominantly released by Th2 cells are IL-4, IL-5, and IL-13. IL-4 and IL-5 are known to mediate antibody isotype switching towards IgE or IgA response, and promote eosinophil recruitment, skewing the immune system toward an "allergic" type of response. Th0 cells release a set of cytokines with characteristics of both Th1-type and Th2-type responses. While the categorization of T cells as Th1, TH2, or Th0 is helpful in describing the differences in immune response, it should be understood that it is more accurate to view the T cells and the responses they mediate as forming a continuum, with Th1 and Th2 cells at opposite ends of the scale, and Th0 cells providing the middle of the spectrum. Therefore, it should be understood that the use of these terms herein is only to describe the predominant nature of the immune response elicited, and is not meant to be limiting to an immune response that is only of the type indicated. Thus, for example, reference to a "type-1" or "Th1" immune response is not meant to exclude the presence of a "type-2" or "Th2" immune response, and vice versa.

Details of in vitro and in vivo techniques useful for evaluation of production of cytokines associated with a type-1 or type-2 response, as well as for evaluation of antibody production, are well known in the art. Likewise, animal models for screening candidate sequences for activity in, for example, reduction of IBD-associated inflammation are also well known in the art, and are further exemplified in the Examples below.

Administration and Dosage

Treatment includes prophylaxis and therapy. Prophylaxis or therapy can be accomplished by a single direct administration at a single time point or multiple time points. Administration can also be delivered to a single or to multiple sites.

The subject can be any vertebrate, but will preferably be a mammal. Mammals include, but are not necessarily limited to, human, bovine, equine, canine, feline, porcine, and ovine animals. If a mammal, the subject will generally be a human, but may also be a domestic livestock, laboratory subject or pet animal. Immunomodulatory nucleic acid molecules are administered to an individual using any available method and route suitable for drug delivery including systemic, mucosal, and localized routes of administration. In general, subjects who receive therapy according to the invention include those who has or are at risk of acute or chronic gastrointestinal inflammation, particularly those who have or are at risk of chronic gastrointestinal inflammation, particularly inflammatory bowel disease, especially ulcerative colitis or Crohn's disease. Methods for identification of such subjects with these conditions or at risk of these conditions are well within the skill and knowledge of the ordinarily skilled artisan.

Routes of administration, dosages, and formulations are described in more detail below.

Routes of Administration

Conventional and pharmaceutically acceptable routes of administration for treatment of gastrointestinal inflammation (e.g., chronic gastrointestinal inflammation such as that of IBD), include, but are not necessarily limited to, intramuscular, subcutaneous, intradermal, transdermal, intravenous, rectal (e.g., enema, suppository), oral, intragastric, intranasal and other routes of effective inhalation routes, and other parenteral routes of administration. In general, gastrointestinal routes of administration are of particular interest in the present invention for treatment of gastrointestinal inflammation including, but not necessarily limited to oral, intranasal, intragastric, and rectal administration. Routes of administration may be combined, if desired, or adjusted depending upon the immunomodulatory nucleic acid molecule and/or the desired effect on the immune response. The immunomodulatory nucleic acid composition can be administered in a single doses, or in multiple doses, and may encompass administration of additional doses, to elicit and/or maintain the desired effect.

Immunomodulatory nucleic acid molecules can be administered to a subject using any available conventional methods and routes suitable for delivery of conventional drugs, including systemic or localized routes. Methods and localized routes that further facilitate production of a type-1 or type-1-like response and/or the anti-gastrointestinal inflammatory (e.g., anti-IBD) activity of the immunomodulatory nucleic acid molecules, particularly at or near a site of inflammation is of interest in the invention, and may be preferred over systemic routes of administration, both for the immediacy of therapeutic effect and reduction of the incident of in vivo degradation of the administered immunomodulatory nucleic acid molecules. In general, routes of administration contemplated by the invention include, but are not necessarily limited to, gastroenteral, enteral, or parenteral routes. Gastroenteral routes of administration include, but are not necessarily limited to, oral and rectal (e.g., using a suppository) delivery.

Dose

The dose of immunomodulatory nucleic acid administrated to a subject, in the context of the present invention, should be sufficient to effect a beneficial therapeutic response in the subject over time, or to alleviate symptoms. Thus, immunomodulatory nucleic acid is administered to a patient in an amount sufficient to alleviate, reduce, cure or at least partially arrest symptoms and/or complications from the disease. An amount adequate to accomplish this is defined as a "therapeutically effective dose."

A particular advantage of therapy using immunomodulatory nucleic acid according to the invention is the capacity of immunomodulatory nucleic acid to exert immunomodulatory activity even at relatively minute dosages. Although the dosage used will vary depending on the clinical goals to be achieved, a suitable dosage range is one which provides up to about 1 μg, to about 1,000 μg, to about 5,000 μg, to about 10,000 μg, to about 25,000,μg or about 50,000 μg of immunomodulatory nucleic acid per ml of carrier in a single dosage. Based on current studies, immunomodulatory nucleic acid is believed to have little or no toxicity at these dosage levels.

It should be noted that the anti-inflammatory and immunotherapeutic activity of immunomodulatory nucleic acid in the invention is essentially dose-dependent. Therefore, to increase immunomodulatory nucleic acid potency by a magnitude of two, each single dose is doubled in concentration. Clinically, it may be advisable to administer the immunomodulatory nucleic acid in a low dosage, then increase the dosage as needed to achieve the desired therapeutic goal (e.g., increasing amounts of immunomodulatory nucleic acid can be administered until a reduction or mitigation in the gastrointestinal inflammation-associated symptom is achieved). In addition, some routes of administration will require higher concentrations than other routes. Those skilled in the art can adjust the dosage and concentration to suit the particular route of delivery.

The effectiveness of therapy can be monitored by monitoring the reduction of disease activity in the subject. Reduction in disease activity can be monitored by, for example, monitoring reduction of incidence of diarrhea or volume of stool, reduction of rectal bleeding, reduction of weight loss, reduction of size or number of colon lesions, reduction or opening of strictures, reduction or closure of fistulae, and the like. Therapeutic effectiveness can also be measured by for example, a decrease in anti-neutrophil cytoplasmic antibodies (ANCA) in a biological sample, a decrease in colonic myclo-peroxidase activity, reduction of anemia (as detected by, for example, erythrocyte sedimentation rate (ESR), hemoglobin levels, and the like), or other conventional indicator of gastrointestinal inflammation. Many of these methods for assessing therapeutic efficacy can be accomplished through endoscopy or through blood tests. Methods for monitoring gastrointestinal inflammation are well known in the art and well within the skill and knowledge of the ordinarily skilled artisan.

Reduction of Risk of Subsequent Disease

The methods of the invention can also provide for reduced risk of other conditions for which gastrointestinal inflammation is a risk factor. For example, ulcerative colitis is a risk factor for colonic carcinoma. Thus, treatment of ulcerative colitis (e.g., by reduction of inflammation) according to the methods of the invention also reduces the risk of colonic cancer (e.g., colonic carcinoma, colonic adenoma, and the like). The methods of the invention can thus be applied as prophylactic measure to prevent or reduce the risk of onset of colonic carcinoma, particularly in those patients that are high risk of colon cancer.

Established risk factors for colon cancer in those patients having ulcerative colitis include long duration of the disease, large extent of the disease, low activity of the disease, young age at onset, presence of complicating primary sclerosing cholangitis or stenotic disease and possibly lack of adequate surveillance, inadequate pharmacological therapy, folate deficiency and non-smoking. Crohn's disease is associated with an increased risk of colorectal carcinoma in patients with long-standing disease, strictures and fistulae under the condition that the colon is involved, tumors of the small intestine may occur occasionally. (see, e.g., Pohl, et al. (2000), ibid). Thus treating using immunomodulatory nucleic acid according to the invention can be of particular benefit in these patients.

Formulations

In general, immunomodulatory nucleic acid molecules are prepared in a pharmaceutically acceptable composition for delivery to a host. Immunomodulatory nucleic acid are optionally provided with a pharmaceutically acceptable carrier. Exemplary pharmaceutically carriers include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition of immunomodulatory nucleic acid may also be lyophilized using means well known in the art, for subsequent reconstitution and use according to the invention. Also of interest are formulations for liposomal delivery, and formulations comprising microencapsulated immunomodulatory nucleic acid molecules.

In general, the pharmaceutical compositions can be prepared in various forms, such as granules, tablets, pills, suppositories, capsules (e.g. adapted for oral delivery), microbeads, microspheres, liposomes, suspensions, salves, lotions and the like. The immunomodulatory nucleic acid useful in the invention can be prepared in a variety of formulations, including conventional pharmaceutically acceptable carriers, and, for example.

Pharmaceutical grade organic or inorganic carriers and/or diluents suitable for oral and topical use can be used to make up compositions comprising the therapeutically-active compounds. Diluents known to the art include aqueous media, vegetable and animal oils and fats. Stabilizing agents, wetting and emulsifying agents, salts for varying the osmotic pressure or buffers for securing an adequate pH value.

Immunomodulatory nucleic acid molecules can be administered in the absence of agents or compounds that might facilitate uptake by target cells (e.g., as a "naked" polynucleotide, e.g., a polynucleotide that is not encapsulated by a viral particle). Immunomodulatory nucleic acid molecules can also be administered with compounds that facilitate uptake of immunomodulatory nucleic acid molecules by cells (e.g., by macrophages) or otherwise enhance transport of the immunomodulatory nucleic acid molecules to a treatment site for action.

Absorption promoters, detergents and chemical irritants (e.g., keratinolytic agents) can enhance transmission of an immunomodulatory nucleic acid molecule composition into a target tissue (e.g., through the skin). For general principles regarding absorption promoters and detergents which have been used with success in mucosal delivery of organic and peptide-based drugs, see, e.g., Chien, *Novel Drug Delivery Systems*, Ch. 4 (Marcel Dekker, 1992). Suitable agents which are known to enhance absorption of drugs through skin are described in Sloan, Use of Solubility Parameters from Regular Solution Theory to Describe Partitioning-Driven Processes, Ch. 5, "Prodrugs: Topical and Ocular Drug Delivery" (Marcel Dekker, 1992), and at places elsewhere in the text. All of these references are incorporated herein for the sole purpose of illustrating the level of knowledge and skill in the art concerning drug delivery techniques.

A colloidal dispersion system may be used for targeted delivery of immunomodulatory nucleic acid molecules to specific tissue. Colloidal dispersion systems include macromolecule complexes, nanocapsules, microspheres, beads, and lipid-based systems including oil-in-water emulsions, micelles, mixed micelles, and liposomes.

Liposomes are artificial membrane vesicles which are useful as delivery vehicles in vitro and in vivo. It has been shown that large unilamellar vesicles (LUV), which range in size from 0.2-4.0 $\mu$m can encapsulate a substantial percentage of an aqueous buffer containing large macromolecules. RNA and DNA can be encapsulated within the aqueous interior and be delivered to cells in a biologically active form (Fraley, et al., (1981) *Trends Biochem. Sci.*, 6:77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

Where desired, targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various well known linking groups can be used for joining the lipid chains to the targeting ligand (see, e.g., Yanagawa, et al., (1988) *Nuc. Acids Symp. Ser.*, 19:189; Grabarek, et al., (1990) *Anal. Biochem.*, 185:131; Staros, et al., (1986) *Anal. Biochem.* 156:220 and Boujrad, et al., (1993) *Proc. Natl. Acad. Sci. USA*, 90:5728). Targeted delivery of immunomodulatory nucleic acid molecules can also be achieved by conjugation of the ISS to the surface of viral and non-viral recombinant expression vectors, to an antigen or other ligand, to a monoclonal antibody or to any molecule which has the desired binding specificity.

Additional Agents

Immunomodulatory nucleic acid for delivery according to the invention can be formulated with additional agents, which agents may be inert or active agents. For example, preservatives and other additives may also be present such as, for example, antimicrobial agents (e.g., antibacterials, antivirals, antifungals, etc.), antioxidants, chelating agents, and inert gases and the like. In addition, the immunomodulatory nucleic acid may be modified to be conjugated to another molecule of interest.

Immunomodulatory nucleic acid can be combined with conventional agents used for treatment of gastrointestinal inflammation, where appropriate. Exemplary agents used in conventional gastrointestinal inflammation therapy, such as those used in therapy for chronic gastrointestinal inflammation such as in IBD, include, but are not necessarily limited to, corticosteroids, azathioprine, cyclosporine, and methotrexate, as well as antibodies directed against tumor necrosis factor-α (TNF-α), or other drug useful in the treatment of chronic gastrointestinal inflammation. Such additional agents can be administered separately or included in the immunomodulatory nucleic acid composition. In addition immunomodulatory nucleic acid can be formulated-with other anti-inflammatory agents, with the proviso that such agents do not substantially interfere with the anti-inflammatory activity of immunomodulatory nucleic acid. Exemplary agents include, but are not necessarily limited to, antacids, H2 blockers, and the like (e.g., famotidine, ranitidine hydrochloride, and the like).

Timing of Administration

Immunomodulatory nucleic acid molecules can be administered to a subject prior to onset of more severe symptoms (e.g., prior to onset of an acute inflammatory attack), or after onset of acute or chronic symptoms (e.g., after onset of an acute inflammatory attack). As such, immunomodulatory nucleic acids can be administered at any time, and may be administered at any interval. In one embodiment, immunomodulatory nucleic acid is administered about 8 hours, about 12 hours, about 24 hours, about 2 days, about 4 days, about 8 days, about 16 days, about 30 days or 1 month, about 2 months, about 4 months, about 8 months, or about 1 year after initial onset of gastrointestinal inflammation-associated symptoms and/or after diagnosis of gastrointestinal inflammation in the subject. As described in more detail below, the invention also provides for administration of subsequent doses of immunomodulatory nucleic acid molecules.

When multiple doses are administered, subsequent doses are administered within about 16 weeks, about 12 weeks, about 8 weeks, about 6 weeks, about 4 weeks, about 2 weeks, about 1 week, about 5 days, about 72 hours, about 48 hours, about 24 hours, about 12 hours, about 8 hours, about 4 hours, or about 2 hours or less of the previous dose. In one embodiment, ISS are administered at intervals ranging from at least every two weeks to every four weeks (e.g., monthly intervals) in order to maintain the maximal desired therapeutic effect (e.g., to provide for maintenance of relief from IBD-associated symptoms).

In view of the teaching provided by this disclosure, those of ordinary skill in the clinical arts will be familiar with, or can readily ascertain, suitable parameters for administration of immunomodulatory nucleic acid according to the invention.

EXAMPLES

The following examples are presented to illustrate the present invention and to assist one of ordinary skill in making and using the same. The examples are not intended in any way to otherwise limit the scope of the invention.

Example 1

Subcutaneous Administration of ISS Ameliorates Symptoms in a Mouse Model of Colitis (DSS-Induced)

In an experiment similar to that of Example 1, groups of Balb/c mice (at least 6 animals per group) were weighed and treated with ISS (10 µg/animal) or M-ODN (10 µg/animal) subcutaneously two hrs prior to induction of colitis by adding dextran sodium sulfate (DSS, Sigma), 2.5% to the drinking water ad libitum. M-ODN is a polynucleotide of the same length as the ISS polynucleotide, but lacking the CpG motif. The polynucleotides used were LPS free, single stranded, 22 mer long, phosphothioate polynucleotides (Trilink, San Diego, Calif.), and had the following sequences:

ISS: 5'-TGACTGTG<u>AACGTT</u>CGAGATGA-3' (SEQ ID NO: 1) and

M-ODN: 5'-TGACTGTG<u>AACCTT</u>AG AGATGA-3' (SEQ ID NO: 3).

Naïve control animals (naïve) received neither DSS nor polynucleotide. Colitis control animals (DSS) received no polynucleotide.

Seven days after induction of colitis, mice were weighed and inspected for diarrhea and rectal bleeding. The mice were sacrificed, and the entire colon was dissected and its length measured and weighed. Scores were again defined as follows:

Changes in body weight: No loss –0; 5 to 10% –1; 10 to 25%, –2; 15 to 20%, –3; >20%–4. Hemoccult: No blood, –0; positive, –2; gross blood, –4. Mucosal samples were processed for determination of MPO activity according to: Bradley J Invest Dermatol (1982) 78: 206-9.

Figure 1D:
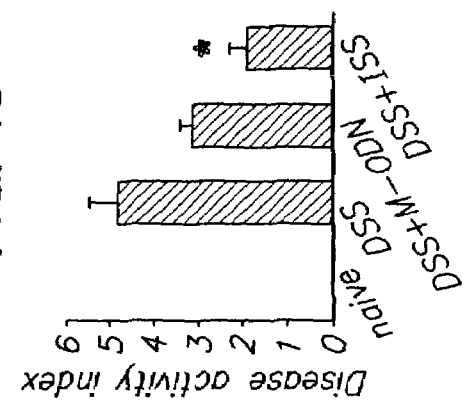

As shown in FIGS. 1A-1D, a single subcutaneous administration of ISS resulted in a decrease in disease activity index (DAI)m (FIG. 1A), the percentage decrease in body weight (FIG. 1B), the colonic weight (FIG. 1C), as well as the decrease in mucosal MPO activity (FIG. 1D).

Example 2

Effect of Various Immunomodulatory Nucleic Acid Sequences on Disease Activity Index in DSS-Induced Colitis ISS (10 μg/animal) mutated control polynucleotides (M-ODN) (10 μg/animal) were injected subcutaneously in Balb/C mice 2 hours prior to DSS administration (2.5%) to drinking water as described in Example 1. The sequences of the various polynucleotides were as follows:

TABLE 1

| Polynucleotide | Sequence | SEQ ID NO: |
| --- | --- | --- |
| 1018 | tgactgtgaacgttcgagatga | 1 |
| 1019 | tgactgtgaaggttagagatga | 4 |
| 1038 | tgactgtgaacgttagagatga | 5 |
| 1039 | tgactgtgaac*gttagagatga | 6 |
| 1042 | tgactgtgttccttagagatga | 2 |
| 1185 | tccatgacgttcctgatgct | 7 |
| 1394 | tgactgtgaatgttagagatga | 8 |
| 1399 | tgactgtggtcgttagagatga | 9 |
| 1401 | tcgtcgtcgtcgtcgtcgtcgt | 10 |
| 1402 | tgaaacgttcgcctgtcgttga | 11 |

Mice were sacrificed 7 days after DSS administration, and disease activity index evaluated. The disease activity index was measured as a combined score of decrease in body weight and the presence of blood in the stool, as described above.

Results are shown in FIG. 2.

Example 3

Dose-Response of Subcutaneous ISS in an Animal Model of Ulcerative Colitis (DSS-Induced)

Figure 3A:
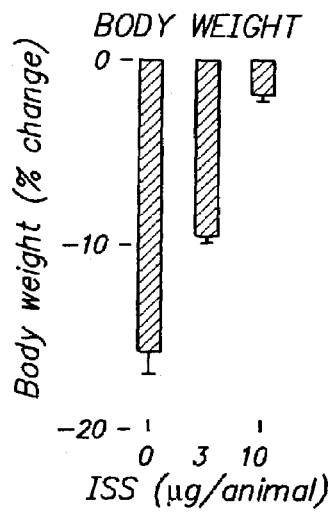
FIGS. 3A-3C are graphs showing the dose-response effect of subcutaneous immunomodulatory polynucleotide administration upon body weight (FIG. 3A), disease activity index (FIG. 3B), and colonic weight (FIG. 3C) in a DSS-induced animal model of colitis.
Figure 3B:
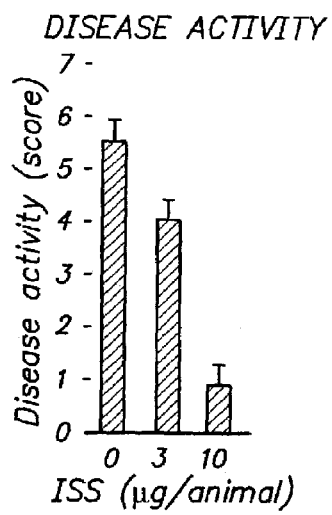
Figure 3C:
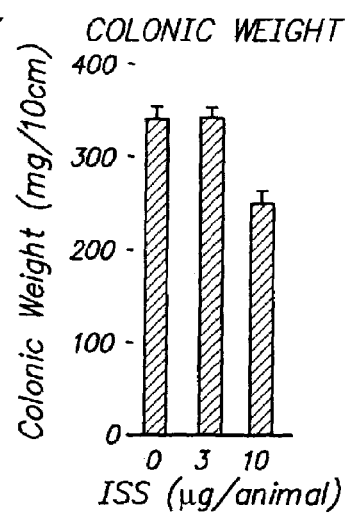

ISS was administered to Balb/c mice subcutaneously as described in Example 1 above at varying doses (0 μg/animal, 3 μg/animal, and 10 μg/animal). Two hours later, DSS was administered by addition to the drinking water ad libitum at a concentration of 2.5%. Seven days after induction of colitis, mice were weighed and inspected for diarrhea and rectal bleeding. The mice were sacrificed, and the entire colon was dissected and its length measured and weighed. Scores were again defined as described in Example 2. The results are provided in FIGS. 3A-3C.

Example 4

Administration of ISS After Onset of Colitis in an Animal Model (DSS-Induced)

DSS was used to induce colitis in Balb/c mice as described in Example 1. ISS or M-ODN (as described in Example 1) was administered at 10 μg/animal 48 hours after DSS exposure. Naïve control animals (naïve) received neither DSS nor polynucleotide. Naïve control animals (naïve) received neither DSS nor polynucleotide. Colitis control animals (DSS) received no polynucleotide.

Seven days after induction of colitis, mice were weighed and inspected for diarrhea and rectal bleeding. The mice were sacrificed, and the entire colon was dissected and its length measured and weighed. Scores were defined as in Example 1.

Figure 4:
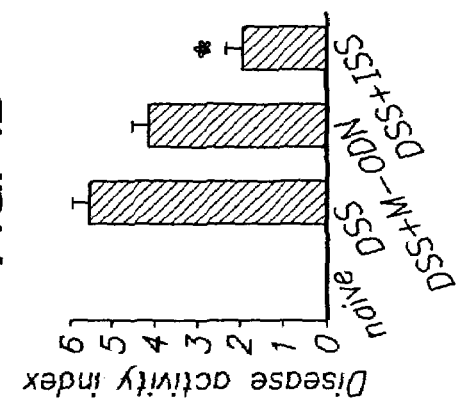
FIG. 4 is a bar graph showing the effect of immunomodulatory polynucleotide upon disease activity index in a DSS-induced animal model of colitis when administered subcutaneously 48 hours after DSS exposure (e.g., in a therapeutic mode).

The results of the effect of ISS administration 48 hrs after DSS exposure are shown in FIG. 4. These results show that, in addition to its protective effects, ISS is also effective in significantly decreasing disease activity index after onset of colitis.

Example 5

ISS in Subsequent DSS Challenge

To evaluate whether the protective effects of ISS on DSS-induced colitis would also protect from subsequent DSS challenge, animals were pre-treated once with ISS (10 μg/animal; ISS as described in Example 1) and exposed to DSS in water (2.5%) for one week. The protective effects of ISS in this group (e.g., disease activity index (DAI) <1) were similar to those obtained with ISS in previous experiments.

DSS was then withdrawn for the following two weeks but afterward it was reintroduced for an additional week. In this group no detectable protective effect for ISS on the second round of DSS-induced colitis were observed (i.e., DAI>5). This finding suggest that long or protracted treatment of gastrointestinal inflammation may require continued immunomodulatory nucleic acid therapy in order to maintain the desired therapeutic effect.

Example 6

Intragastric Administration of ISS Ameliorates Symptoms in a Mouse Model of Colitis Balb/c mice were treated with 30 μg/animal of ISS or M-ODN (as described in Example 2) by intragastric administration. Two hours later, the animals were treated with DSS to induce colitis as described in Example 2 above. Naïve control animals (naïve) received neither DSS nor polynucleotide. Colitis control animals (DSS) received no polynucleotide. Seven days after induction of colitis, mice were weighed and inspected for diarrhea and rectal bleeding. The mice were sacrificed, and the entire colon was dissected and its length measured and weighed. Scores were defined as described in Example 2.

Figure 5:
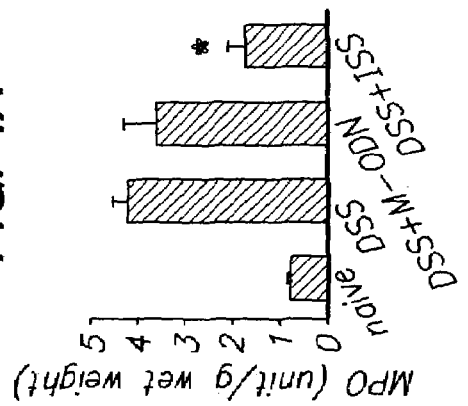
FIG. 5 is a graph showing the effects of administration of intragastric immunomodulatory polynucleotide two hours prior to induction of colitis by administration of DSS in an animal model.

The results are shown in FIG. 5. This experiment shows that ISS exhibits a protective effect when administered intragastrically.

Example 7

Dose-Response of Intragastric ISS in an Animal Model of Ulcerative Colitis (DSS-Induced)

Figure 6A:
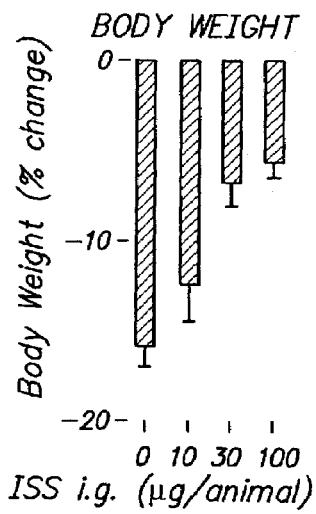
FIGS. 6A-6C are graphs showing the dose-response effect of intragastric immunomodulatory polynucleotide administration upon body weight (FIG. 6A), disease activity index (FIG. 6B), and colonic weight (FIG. 6C) in a DSS-induced animal model of colitis.
Figure 6B:
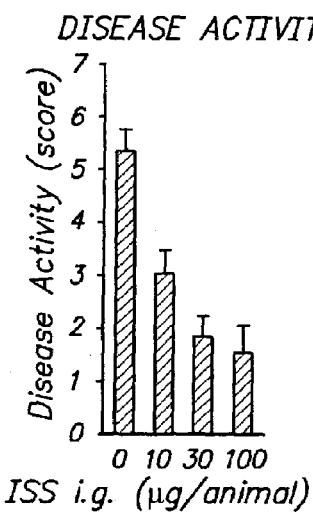
Figure 6C:
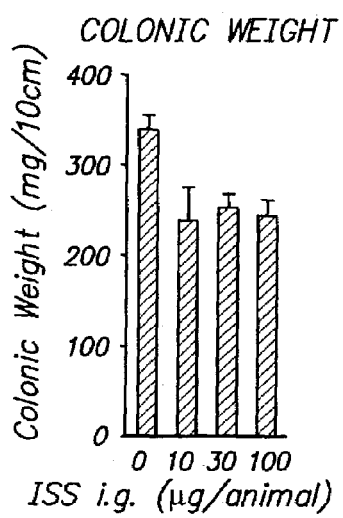

ISS was administered to Balb/c mice intragastrically as described in Example 1 above at varying doses (0 μg/animal, 10 μg/animal, 30 μg/animal, and 100 μg/animal). Two hours later, DSS was administered by addition to the drinking water ad libitum at a concentration of 2.5%. Seven days after induction of colitis, mice were weighed and inspected for diarrhea and rectal bleeding. The mice were sacrificed, and the entire colon was dissected and its length measured and weighed. Scores were again defined as described in Example 1. The results are provided in FIGS. 6A-6C.

Example 8

PCR Analysis of the Effect of ISS Upon Colonic Tissue from DSS-Induced Inflammation To evaluate the anti-inflammatory role of ISS on DSS-induced colitis, a single administration of ISS or M-ODN (10 μg/mouse; polynucleotides as described in Example 2) was delivered subcutaneously 2 hrs prior to DSS challenge as described in Example 2. Mice were sacrificed 7 days later.

mRNAs were isolated from colonic and duodenal sections (5 mm per section) using Micro-FastTrack mRNA isolation kit [Invitrogen]. After isolation of mRNAs reverse transcriptase reactions were performed using SuperScrip™ First-strand synthesis system [GibcoBRL] according to a manufacture's protocol. Generated cDNAs were applied to PCR analysis for gene regulation of chemokines, cytokines and metalloproteinases. The following sets of oligonucleotides were used as primers for the indicated chemokines, cytokines, and metalloproteinases:

```
1)  IL-1β    (sense)      5'-ATGAGCTTTGTACAAGCIAGAAC2CA-3'   (SEQ ID NO:12)
             (anti-sense) 5'-TTAGGAAGACACAGATTCCATGGT-3'     (SEQ ID NO:13)

2)  IFN-γ    (sense)      5'-GGTGACATGAAAATCCTGCAGAGC-3'    (SEQ ID NO:14)
             (anti-sense) 5'-TCAGCAGCGACTCCTTTTCCGCTT-3'    (SEQ ID NO:15)

3)  IL-12/p40 (sense)     5'-GGGACATCATCAAACCAGACC-3'       (SEQ ID NO:16)
             (anti-sense) 5'-GCCAACCAAGCAGAAGACAGC-3'       (SEQ ID NO:17)

4)  TGFβ     (sense)      5'-GATACCAACTATTGCTTCAGCTCCACA-3' (SEQ ID NO:18)
             (anti-sense) 5'-TCAGCTGCACTTGCAGGAGCGCACAAT-3' (SEQ ID NO:19)

5)  TNTα     (sense)      5'-ATCAGTTCTATGGCCCAGACCCTCACA-3' (SEQ ID NO:20)
             (anti-sense) 5'-TCACAGAGCAATGACTCCAAAGTAGAG-3' (SEQ ID NO:21)

6)  MCP-2    (sense)      5'-ATGAAGATCTACGCAGTGCTTCTTTGC-3' (SEQ ID NO:22)
             (anti-sense) 5'-TCAAGGCTGCAGAATTTGAGACTTCTG-3' (SEQ ID NO:23)

7)  MCP-3    (sense)      5'-ATGAGGATCTCTGCCACGCTTCTGTGC-3' (SEQ ID NO:24)
             (anti-sense) 5'-AGGCTTTGGAGTTGGGGTTTTCATGTC-3' (SEQ ID NO:25)

8)  MIP-2    (sense)      5'-ATGGCCCCTCCCACCTGCCGGCTCCTC-3' (SEQ ID NO:26)
             (anti-sense) 5'-AGGTACGATCCAGGCTTCCCGGGTGCT-3' (SEQ ID NO:27)

9)  KC       (sense)      5'-ATGATCCCAGCCACCCGCTCGCTTCTC-3' (SEQ ID NO:28)
             (anti-sense) 5'-TTACTTGGGGACACCTTTTAGCATCTT-3' (SEQ ID NO:29)

10) MMP-1    (sense)      5'-AACAAATACTGGAAGTTCAACAAC-3'    (SEQ ID NO:30)
             (anti-sense) 5'-TCAGACCTTGTCCAGCAGCGAACG-3'    (SEQ ID NO:31)

11) MMP-3    (sense)      5'-AAGGGGATCCCTGAATCACCTCAG-3'    (SEQ ID NO:32)
             (anti-sense) 5'-TCACACCCACTCTTGCATAGACCG-3'    (SEQ ID NO:33)

12) MMP-9    (sense)      5'-TGGTACTGGAAGTTCCTGAATCATAGA-3' (SEQ ID NO:34)
             (anti-sense) 5'-CAAGGGCACTGCAGGAGGTCGTAGGTC-3' (SEQ ID NO:35)

13) MMP-10   (sense)      5'-GCAGTCCGAGGANATGAAGTCCAA-3'    (SEQ ID NO:36)
             (anti-sense) 5'-TCAGCACAGCAGCCAGCTGTTGCT-3'    (SEQ ID NO:37)

14) G3PDH    (sense)      5'-ACCACAGTCCATGCCATCAC-3'        (SEQ ID NO:38)
             (anti-sense) 5'-TCCACCACCCTGTTGCTGTA-3'        (SEQ ID NO:39)
```

PCR was performed with 1 μl of RT mix, 20 pmol of each sense and anti-sense primer, 0.2 mM dNTPs, 2.5 mM $MgCl_2$ and 2 units of Taq DNA polymerase to a final volume of 30 μl. The PCR cycling parameters were 94° C. (30 sec), 68° C. (1 min) for 18 cycles and 24 cycles for G3PDH and for other test genes, respectively. PCR products were separated on 1.5% agarose-gel and visualized by ethidium bromide staining.

Western blot analysis of MMP-10 levels was performed on colonic tissues obtained from naive, DSS, DSS+M-ODN and DSS+ISS treated mice. Lysates (40 μg) were separated on 10-20% Tricine SDS-PAGE, blotted on PVDF membrane and stained with rabbit anti-mouse MMP-10 or rabbit anti-mouse IL-1β antibodies (Chemicon, Tamecula Calif.).

Results are shown in FIGS. 7A-7F. Data shown represent one of three similar experiments with identical results. FIG. 7A shows that ISS induces IL-12 and IFN-γmRNA in colonic tissue of naïve animals. FIGS. 7B- 7D illustrate ISS inhibition of the induction of DSS-induced IL-1β and TNF-α(FIG. 7B), the induction of chemokines such as; MCP-2. MIP-2 and KC (FIG. 7C), and the induction of matrix metalloproteinases such as; MMP-1, MMP-3, MMP-9 and MMP-10 (FIG. 7D). ISS also inhibited MMP-10 induction, as shown by Western blot analysis (FIG. 7E). ISS administration did not affect the expression of IL-1β, KC and MMP-10 in the duodenum of DSS-treated mice (FIG. 7F).

Example 9

In Vivo Analysis of ISS Inhibition of DSS-Induced Inflammation and Cell Death

In order to evaluate whether ISS enhances mucosal restitution, the extent of colonic epithelial cell death in ISS treated mice was evaluated both histologically and using the TUNEL assay. Mice were treated with 10 μg/animal polynucleotide (ISS or control M-ODN as per Example 2) subcutaneously or with 30 μg/animal ISS, and DSS administered two hours later as described in Example 2. Seven days after DSS administration, the animals were sacrificed, and tissue sections (colon) were collected.

For histological analysis, the tissue sections were fixed overnight in 10% buffered formalin at room temperature and embedded in paraffin. The paraffin-embedded tissue section were further sectioned (5–μm thickness), stained with hematoxylin-eosin (H&E staining). Exemplary results are shown in FIGS. 8A-8D: FIG. 8A, control (no DSS, no polynucleotide); FIG. 8B, DSS alone; FIG. 8C, DSS and subcutaneous control M-ODN; FIG. 8D, DSS and subcutaneous ISS; and FIG. 8E, DSS and intragastric ISS.

In order to evaluate apoptosis of intestinal cells, apoptotic cells were detected in situ by the terminal deoxynucleotidyl transferase-mediated d-UTP nick end labeling (TUNEL) assay. Samples were labeled with in situ cell death detection kit (fluorescein; Roche Molecular Biochemical. Indianapolis, Ind.) according to the manufacture's instruction and observed under a fluorescent microscope (Olympus Optical Co., Lake Success, N.Y.). Three specimens from each colon were evaluated, and representative fields were photographed with an Olympus camera, equipped with a Sony DKC5000 charge-coupled device. The images were captured and processed for presentation with Adobe Photoshop 5.5 and printed on a dye sublimation printer. Exemplary results are shown in FIGS. 9A-9D: Figure, control (no DSS, no polynucleotide); FIG. 9B, DSS alone; FIG. 9C, DSS and subcutaneous control M-ODN: FIG. 9D, DSS and subcutaneous ISS; and FIG. 9E, DSS and intragastric ISS.

H&E staining demonstrated shortening of the epithelial crypts and thinning of epithelium, significant cellular infiltration in the lamina propria, and submucosal edema in the colon from DSS or M-ODN-treated mice. Colonic architecture is preserved and cellular infiltration is markedly reduced in DSS+ISS treated mice. TUNEL assays were negative in ISS treated mice and markedly positive in the control groups, as indicated by the multiple TUNEL positive cells at the colonic villous tip from DSS or from M-ODN-treated mice. These findings coincide with the histological evaluation of colonic tissue that revealed normal mucosa and inflamed mucosa in ISS and control groups, respectively.

Example 10

In Vitro Analysis of ISS Inhibition of DSS-Induced Inflammation and Cell Death

To further evaluate the effect of ISS on DSS-induced cell death in vitro, bone marrow derived macrophages (BMDM) were cultured as described (Martin-Orozco et al. Int Immunol (1999) 11:1111-8) for 7 days and then incubated with 0.1% DSS in the presence or absence of ISS (1 μg/ml) or control M-ODN (1 μg/ml). ISS or control M-ODN were added 2 hrs prior to treatment with DSS. BMDM cultured without DSS or ISS served as a control. Effects of ISS were also compared to caspase activity induced by the apoptosis inhibitor ZVAD (50 mM).

Catalytic activity of the pro-apoptosis caspases, caspase 3 and 9, was measured in cell lysates using fluorometric substrates, the caspase-3-like Ac-DEVD-AMC and the caspase-9-like Ac-LEHD-AFC, as described by Genini D et al., Blood (2000) 96:3537-43.

Figure 10A:
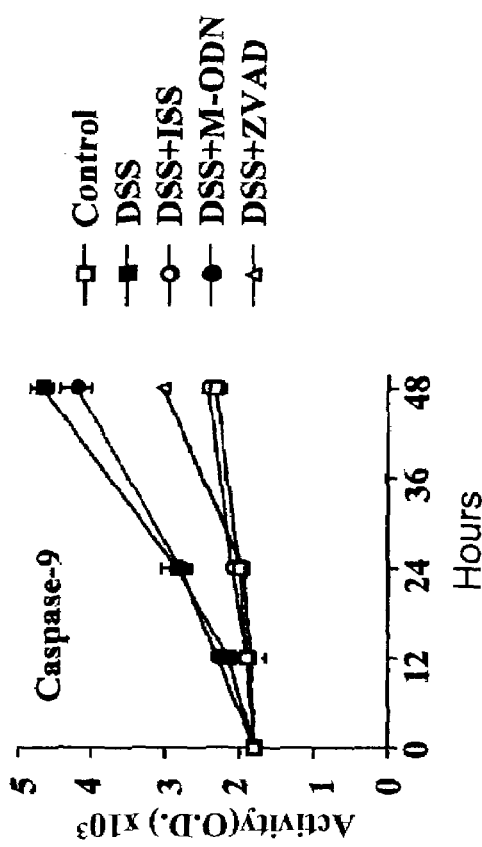
FIGS. 10A and 10B are graphs showing Caspase-3 and Caspase-9 activity, respectively, in bone marrow derived macrophages cultured in media alone (Control, open squares), with DSS (closed squares), DSS and immunomodulatory polynucleotide (open circles), DSS and control M-ODN (closed circles), and DSS and ZVAD, a synthetic inhibitor of caspases (open triangles).
Figure 10B:
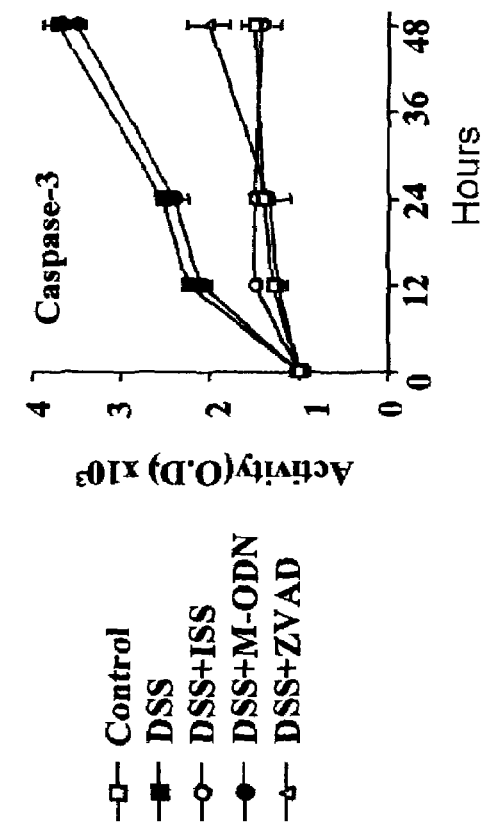

As shown in FIGS. 10A and 10B, respectively, caspase 3 and caspase 9 activities were significantly lower in the ISS treated group in comparison to the DSS or to the DSS+M-ODN treated groups ($p<0.05$, Students' t test). Data shown represent one of three experiments with similar results. These data indicate that ISS protects cells from apoptosis.

Example 11

ISS Ameliorates DNB-Induced Colitis

Colitis was induced in Balb/c mice by rectal instillation of 2,4,6-dinitrobenzene sulfonic acid (DNBS) at 1 mg/mouse, dissolved in 0.1 ml of 50% ethanol. Treated animals received subcutaneous ISS or M-ODN (as described in Example 1; 10 μg/animal) two hrs prior to induction of colitis or 48 hrs after induction of colitis. Mice were sacrificed seven days after DNBS administration. Disease activity index and MPO activity were determined as in DSS induced colitis (see above). Data represent means±SE. There are at least 6 mice per group. Panels A-D represent one experiment out of two, which were performed. * denotes $p<0.05$ of ISS or M-ODN treated groups in comparison to the DNBS group (Students' t test for unpaired data, the non-parametric Mann Whitney test and Chi Square test).

Figure 11A:
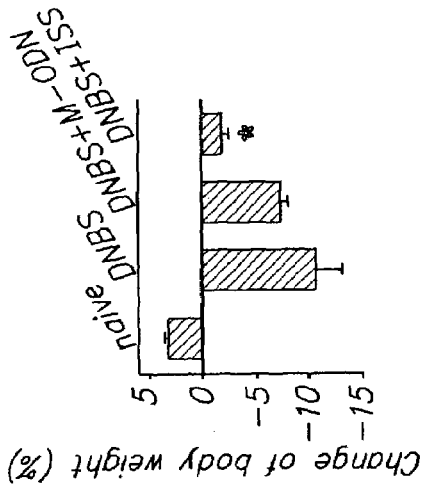
FIGS. 11A-11F are graphs showing the effects of immunomodulatory polynucleotide upon DNBS-induced colitis. Immunomodulatory polynucleotide was administered subcutaneously 2 hours prior to DNBS challenge in FIGS. 11A-E. Immunomodulatory polynucleotide was administered 48 hrs after DNBS challenge in FIG. 11F.
Figure 11B:
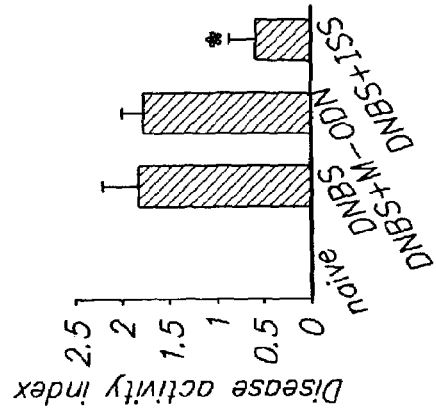
Figure 11C:
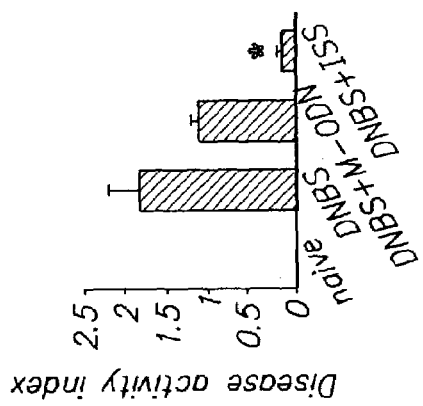
Figure 11D:
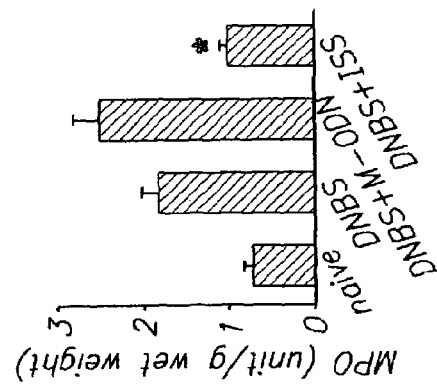
Figure 11E:
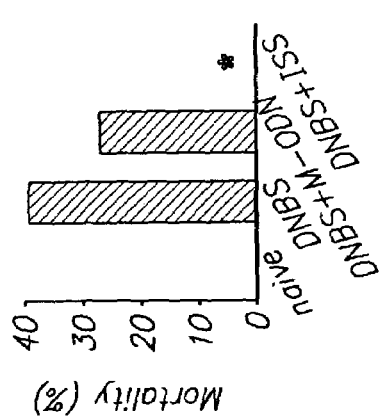

As shown in FIGS. 11A-11E, ISS treatment rescued mice from DNBS-induced death (FIG. 11A). The disease activity index (DAI) (FIG. 11B), change in body weight (FIG. 11C), colonic weight (FIG. 11D), and colonic MPO activity (FIG. 11E) were also reduced in ISS treated animals in comparison to mice in the other group which survived DNBS challenge.

Figure 11F:
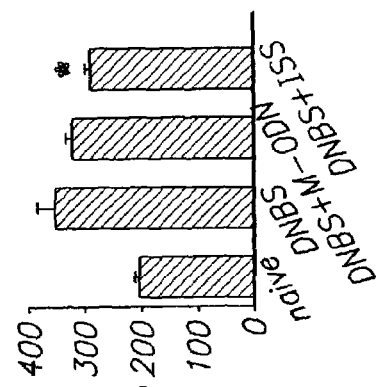
Figures 12A, 12B, 12C, 12D:
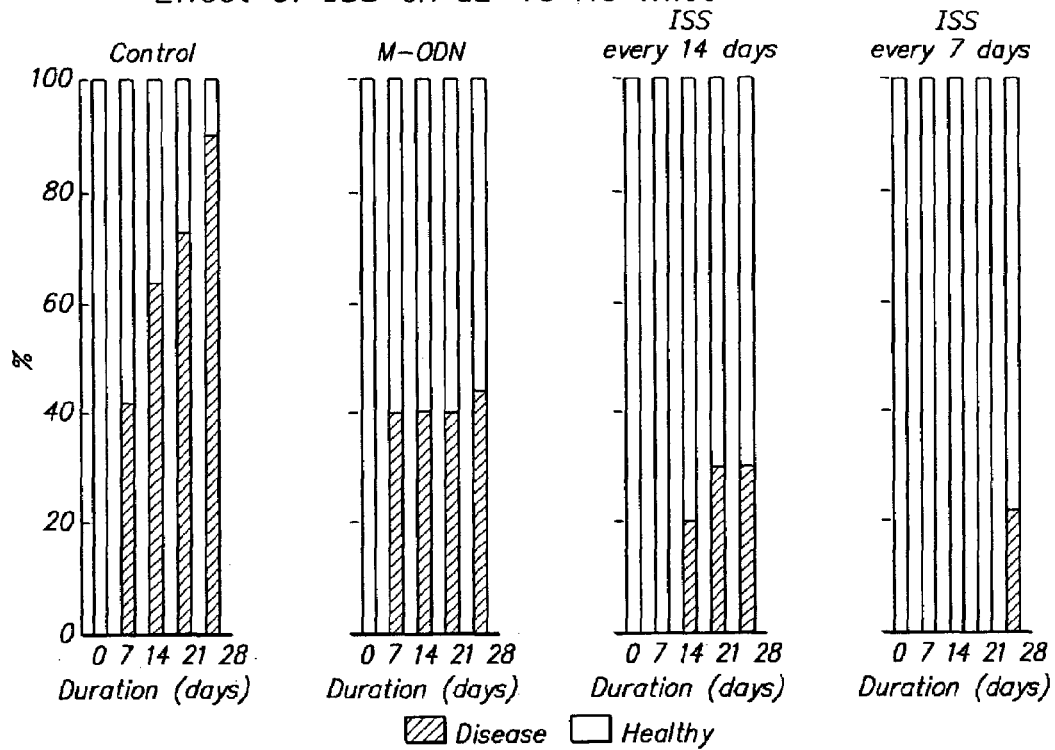
FIGS. 12A-12D are graphs showing the effects o immunomodulatory polynucleotide upon spontaneous colitis in IL-10 knockout transgenic mice. Immunomodulatory polynucleotide (ISS) was administered every 14 days (FIG. 12C) or every 7 days (FIG. 12D). Control represents untreated animals (FIG. 12A). The effects of control M-ODN delivered every 7 days are presented in FIG. 12B. The dark portion of the bars represent the number of animals in the group presenting with disease, while the gray-shaded portion represents the percentage of animals that were healthy at the indicated timepoints.

ISS administration 48 hrs after induction of colitis also resulted in reduced DAI (FIG. 11F).

Example 12

Effect of Immunomodulatory Nucleic Acid Upon Spontaneous IBD in an IL-10 Knockout Mouse (IL-10 KO)

Six week old IL-10 KO mice (Bhan et a. Immunol Rev (1999) 169:195-207) were treated subcutaneously with M-ODN (50 μg/animal) or ISS (50 μg/animal) every 7 days (ISS and M-ODN) or 14 days (ISS). Mice were followed for 4 weeks and the presence of disease reflected by rectal protrusion and bleeding was monitored. The results are shown in FIGS. 12A-12D. The dark portion of the bars represent the number of animals in the group presenting with disease, while the grey-shaded portion represents the percentage of animals that were healthy at the indicated timepoints.

Example 13

Effect of Genomic Bacterial DNA on DSS-Induced Colitis

Colitis was induced in mice by adding DSS 2.5% to the drinking water. Mice were treated 2 hours prior to the addition of DSS with 50 μg/animal of lactobacillus (VSL) DNA, *E. coli* DNA, or calf thymus DNA (thymus). The DNA was isolated as whole genomic DNA from each of these sources and was detoxified from LPS using methods well known in the art.

Figures 13A, 13B:
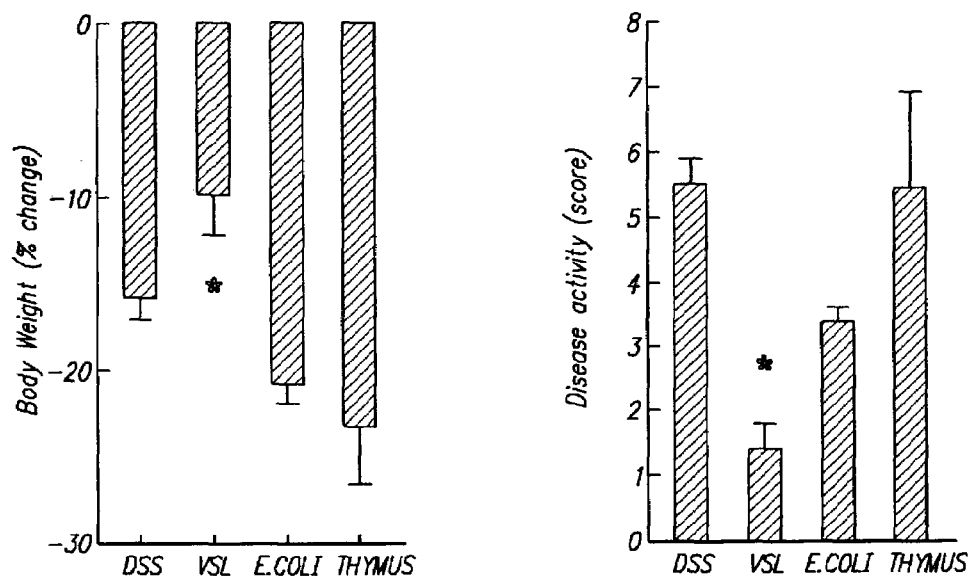
FIGS. 13A-13B are graphs showing the effect of lactobacillus (VSL) genomic DNA, *E. coli* genomic DNA, or control calf thymus DNA (thymus) upon body weight (FIG. 13A) and disease activity index (FIG. 13B) in an DSS-induced animal model of colitis.

Mice were sacrificed after 7 days. Disease activity was measured using the disease activity index described above, a combined score of decrease in body weight and the presence of blood in the stool. The results are shown in FIGS. 13A-13B. The asterisk indicates significance at the p<0.05 confidence level. These data demonstrate that genomic bacterial DNA can ameliorate colitis.

Example 14

ISS Inhibits Spontaneous Release of Inflammatory Mediators from Colonic Mucosa of IBD Patients To evaluate whether the effects of ISS observed in the two models of experimental colitis are applicable to the human, colonic biopsies were obtained from patients with active ulcerative colitis or Crohn's colitis and organ cultured for 24 hours in the presence of ISS or M-ODN (10 μg of each) as previously described by Sharon P. et al Gastroenterology (1978) 65; 638-40. The accumulation in the medium of IFNγ and IL-1β were determined by ELISA (Biosource International, Camarillo, Calif.).

As shown in Table 2, ISS inhibit IL-1β and stimulate IFNα generation suggesting that the anti-inflammatory effects of ISS observed in mice are operating in the human. IFNα and IL-β levels in ODN free media were 1.6±0.4 and 35.5±10 pg/mg of wet weight (mean±SE), respectively, and were considered as 100%. * denotes p<0.05 in comparison to IFNγ or IL-β generation obtained in ODN free media (Student's t test).

TABLE 2

Effect of ISS-ODN on hIFNγ and hIL-β generation by colonic mucosa of IBD patients.

| Treatment | Number of patients | hIFNγ(%) | hIL-1β(%) |
|---|---|---|---|
| ISS-ODN | 10 | 203 ± 37* | 45 ± 7* |
| M-ODN | 7 | 103 ± 14 | 119 ± 15 |

Those skilled in the art will appreciate that the conceptions and specific embodiments disclosed in the foregoing description may be readily utilized as a basis for modifying or designing other embodiments for carrying out the same purposes of the present invention.

What is claimed is:

1. A method for ameliorating gastrointestinal inflammation in a subject comprising:

administering to a subject suffering from gastrointestinal inflammation a formulation comprising an immunomodulatory nucleic acid to the subject, wherein said immunomodulatory nucleic acid is isolated or synthetic, wherein the immunomodulatory nucleic acid comprises a nucleotide sequence selected from:

a) Purine-Purine-[C]-[G]-Pyrimidine-Pyrimidine-3';
b) 5'-Purine-TCG-Pyrimidine-Pyrimidine-3';
c) 5'-[TCG]$_n$-3', where n is any integer that is 1 or greater;
d) 5'-Purine-Purine-CG-Pyrimidine-Pyrimidine-CG-3'; and
e) 5'-Purine-TCG-Pyrimidine-Pyrimidine-CG-3', said administering being in an amount effective to ameliorate a symptom of gastrointestinal inflammation in the subject;

wherein gastrointestinal inflammation is ameliorated in the subject.

2. The method of claim 1, wherein the immunomodulatory nucleic acid comprises the sequence 5'-Purine-Purine-[C]-[G]-Pyrimidine-Pyrimidine-3'.

3. The method of claim 1, wherein the immunomodulatory nucleic acid molecule comprises a CpG motif selected from the group consisting of:

a) 5'-Purine-TCG-Pyrimidine-Pyrimidine-3';
b) 5'-[TCG]$_n$-3', where n is any integer that is 1 or greater;
c) 5'-Purine-Purine-CG-Pyrimidine-Pyrimidine-CG-3'; and
d) 5'-Purine-TCG-Pyrimidine-Pyrimidine-CG-3'.

4. The method of claim 1, wherein the immunomodulatory nucleic acid molecule is selected from the group consisting of an immunostimulatory oligodeoxyribonucleotide (ISS-ODN); an isolated bacterial genomic DNA, and plasmid DNA comprising an immunomodulatory nucleic acid sequence.

5. The method of claim 1, wherein the immunomodulatory nucleic acid molecule comprises a sequence selected from the group consisting of: AACGCC, AACGCT, AACGTC, AACGTT, AGCGCC, AGCGCT, AGCGTC, AGCGTT, GACGCC, GACGCT, GACGTC, GACGTT, GGCGCC, GGCGCT, GGCGTC, GGCGTT, ATCGCC, ATCGCT, ATCGTC, ATCGTT, GTCGCC, GTCGCT, GTCGTC, GTCGTT, TCGTCG, TCGTCGTCG, AACGCCCG, AACGCTCG, AACGTCCG, AACGTTCG, AGCGCCCG, AGCGCTCG, AGCGTCCG, AGCGTTCG, GACGCCCG, GACGCTCG, GACGTCCG, GACGTTCG, GGCGCCCG, GGCGCTCG, GGCGTCCG, GGCGTTCG, ATCGCCCG, ATCGCTCG, ATCGTCCG, ATCGTTCG, GTCGCCCG, GTCGCTCG, GTCGTCCG, and GTCGTTCG.

6. The method of claim 4, wherein the immunomodulatory nucleic acid molecule comprises at least one sequence selected from the group consisting of AACGTT, aacgttcg, aacgtt, gtcgtt, and tcgtcg.

7. The method of claim 4, wherein the immunomodulatory nucleic acid molecule comprises at least one sequence selected from the group consisting of tgactgtgaacgttcgagatga (SEQ ID NO: 1), tgactgtgaacgttagagatga (SEQ ID NO:5), tgactgtggtcgttagagatga (SEQ ID NO:9), tcgtcgtcgtcgtcgtcgt (SEQ ID NO:10), and tgaaacgttcgcctgtcgttga (SEQ ID NO:11).

8. The method of claim 1, wherein the immunomodulatory nucleic acid is administered via a gastroenteral route.

9. The method of claim 1, wherein the gastroenteral route is oral, intranasal, intragastric or rectal.

10. The method of claim 1, wherein the immunomodulatory nucleic acid is administered by a systemic route.

11. The method of claim 10, wherein the systemic route is intradermal, intramuscular, subcutaneous or intravenous.

12. The method of claim 1, wherein the immunomodulatory nucleic acid is administered by a mucosal route.

13. The method of claim 1, wherein the gastrointestinal inflammation is chronic gastrointestinal inflammation.

14. The method of claim 13, wherein the chronic gastrointestinal inflammation is caused by inflammatory bowel disease.

15. The method of claim 14, wherein the inflammatory bowel disease is ulcerative colitis.

16. The method of claim 14, wherein the inflammatory bowel disease is Crohn's disease.

17. The method of claim 14, wherein the immunomodulatory nucleic acid is administered in conjunction with a steroid or an antibody directed against tumor necrosis factor-α (TNF-α).

18. The method of claim 1, wherein the gastrointestinal inflammation is acute gastrointestinal inflammation.

19. A method for ameliorating inflammatory bowel disease in a subject comprising:
administering to a subject suffering from inflammatory bowel disease a formulation comprising an immunomodulatory nucleic acid to the subject, the immunomodulatory nucleic acid comprising the sequence 5'-Purine-Purine-[C]-[G]-Pyrimidine-Pyrimidine-3', said administering being in an amount effective to ameliorate a symptom of inflammatory bowel disease in the subject;
wherein inflammatory bowel disease is ameliorated in the subject.

20. The method of claim 19, wherein said administering is by an intragastric route.

21. The method of claim 19, wherein said administering is by a subcutaneous route.

22. A method for ameliorating inflammatory bowel disease in a subject comprising:
administering to a subject suffering from inflammatory bowel disease a formulation comprising an immunomodulatory nucleic acid to the subject, the immunomodulatory nucleic acid comprising at least one sequence selected from the group consisting of tgactgtgaacgttcgagatga (SEQ ID NO:1), tgactgtgaacgttagagatga (SEQ ID NO:5), tgactgtggtcgttagagatga (SEQ ID NO:9), tcgtcgtcgtcgtcgtcgt (SEQ ID NO:10), and tgaaacgttcgcctgtcgttga (SEQ ID NO:11), said administering being in an amount effective to ameliorate a symptom of inflammatory bowel disease in the subject.

23. A method for reducing inflammation caused by a gastrointestinal inflammatory disease in a subject, the method comprising:
administering to a subject suffering from gastrointestinal inflammatory disease a formulation comprising an immunomodulatory nucleic acid to the subject, wherein said immunomodulatory nucleic acid is isolated or synthetic, said administering being in an amount effective to reduce inflammation caused by gastrointestinal inflammatory disease in the subject;
wherein the immunomodulatory nucleic acid comprises a nucleotide sequence selected from:
a) Purine-Purine-[C]-[G]-Pyrimidine-Pyrimidine-3';
b) 5'-Purine-TCG-Pyrimidine-Pyrimidine-3';
c) 5'-[TCG]$_n$-3', where n is any integer that is 1 or greater;
d) 5'-Purine-Purine-CG-Pyrimidine-Pyrimidine-CG-3'; and
e) 5'-Purine-TCG-Pyrimidine-Pyrimidine-CG-3',
wherein inflammation caused by gastrointestinal inflammatory disease is reduced in the subject.

24. The method of claim 23, wherein the immunomodulatory nucleic acid comprises the sequence 5'-Purine-Purine-[C]-[G]-Pyrimidine-Pyrimidine-3'.

25. The method of claim 23, wherein the immunomodulatory nucleic acid molecule comprises a CpG motif selected from the group consisting of:
a) 5'-Purine-TCG-Pyrimidine-Pyrimidine-3';
b) 5'-[TCG]$_n$-3', where n is any integer that is 1 or greater;
c) 5'-Purine-Purine-CG-Pyrimidine-Pyrimidine-CG-3'; and
d) 5'-Purine-TCG-Pyrimidine-Pyrimidine-CG-3'.

26. The method of claim 23, wherein the immunomodulatory nucleic acid molecule is selected from the group consisting of an immunostimulatory oligodeoxyribonucleotide (ISS-ODN); an isolated, detoxified bacterial polynucleotide; bacterial genomic DNA; and a plasmid DNA comprising an immunomodulatory nucleic acid.

27. The method of claim 23, wherein the inmiunomodulatory nucleic acid molecule comprises a sequence selected from the group consisting of: AACGCC, AACGCT, AACGTC, AACGTT, AGCGCC, AGCGCT, AGCGTC, AGCGTT, GACGCC, GACGCT, GACGTC, GACGTT, GGCGCC, GGCGCT, GGCGTC, GGCGTT, ATCGCC, ATCGCT, ATCGTC, ATCGTT, GTCGCC, GTCGCT, GTCGTC, GTCGTT, TCGTCG, TCGTCGTCG, AACGCCCG, AACGCTCG, AACGTCCG, AACGTTCG, AGCGCCCG, AGCGCTCG, AGCGTCCG, AGCGTTCG, GACGCCCG, GACGCTCG, GACGTCCG, GACGTTCG, GGCGCCCG, GGCGCTCG, GGCGTCCG, GGCGTTCG, ATCGCCCG, ATCGCTCG, ATCGTCCG, ATCGTTCG, GTCGCCCG, GTCGCTCG, GTCGTCCG, and GTCGTTCG.

28. The method of claim 23, wherein the immunomodulatory nucleic acid molecule comprises the sequence at least one sequence selected from the group consisting of aacgtt, aacgttcg, aacgtt, gtcgtt, and tcgtcg.

29. The method of claim 23, wherein the immunomodulatory nucleic acid comprises at least one sequence selected from the group consisting of tgactgtgaacgttcgagatga (SEQ ID NO:1), tgactgtgaacgttagagatga (SEQ ID NO:5), tgactgtgtcgttagagatga (SEQ ID NO:9), tcgtcgtcgtcgtcgtcgtcgt (SEQ ID NO:10), and tgaaacgttcgcctgtcgttga (SEQ ID NO:11).

30. The method of claim 23, wherein the immunomodulatory nucleic acid is administered via a gastroenteral route.

31. The method of claim 30, wherein the gastroenteral route is oral, intranasal, intragastric or rectal.

32. The method of claim 23, wherein the immunomodulatory nucleic acid is administered by a systemic route.

33. The method of claim 32, wherein the systemic route is intradermal, intramuscular, subcutaneous or intravenous.

34. The method of claim 23 wherein the immunomodulatory nucleic acid is administered by a mucosal route.

35. The method of claim 23, wherein the gastrointestinal inflammation is chronic gastrointestinal inflammation.

36. The method of claim 33, wherein the chronic gastrointestinal inflammation is caused by inflammatory bowel disease.

37. The method of claim 36, wherein the immunomodulatory nucleic acid is administered in conjunction with a steroid or an antibody directed against tumor necrosis factor-α (TNF-α).

38. The method of claim 35, wherein the chronic gastrointestinal inflammatory disease is ulcerative colitis.

39. The method of claim 35, wherein the chronic gastrointestinal inflammatory disease is Crohn's disease.

40. A method for reducing inflammation caused by inflammatory bowel disease in a subject comprising:
    administering to a subject suffering from inflammatory bowel disease a formulation comprising an immunomodulatory nucleic acid to the subject, the immunomodulatory nucleic acid comprising the sequence 5'-Purine-Purine- [C]-[G]-Pyrimidine-Pyrimidine-3', said administering being in an amount effective to reduce inflammation caused by inflammatory bowel disease in the subject;
    wherein inflammation caused by inflammatory bowel disease is reduced in the subject.

41. The method of claim 40, wherein said administering is by an intragastric route.

42. The method of claim 40, wherein said administering is by a subcutaneous route.

43. The method of claim 40, wherein the inflammatory bowel disease is ulcerative colitis.

44. The method of claim 40, wherein reduction of inflammation of ulcerative colitis further decreases the risk of colonic carcinoma.

45. The method of claim 43, wherein the inflammatory bowel disease is Crohn's disease.

46. A method for reducing inflammation of inflammatory bowel disease in a subject comprising:
    administering to a subject suffering from inflammatory bowel disease a formulation comprising an immunomodulatory nucleic acid to the subject, the immunomodulatory nucleic acid comprising at least one sequence selected from the group consisting of tgactgtgaacgttcgagatga (SEQ ID NO:1), tgactgtgaacgttagagatga (SEQ ID NO:5), tgactgtggtcgttagagatga (SEQ ID NO:9), tcgtcgtcgtcgtcgtcgt (SEQ ID NO:10), and tgaaacgttcgcctgtcgttga (SEQ ID NO:11), said administering being in an amount effective to reduce inflammation in the subject;
    wherein inflammation caused by inflammatory bowel disease is reduced in the subject.

* * * * *